United States Patent
Pearlman et al.

(10) Patent No.: US 11,779,634 B2
(45) Date of Patent: *Oct. 10, 2023

(54) FUNGAL IRON ACQUISITION INHIBITORS AND USES THEREOF

(71) Applicant: CASE WESTERN RESERVE UNIVERSITY, Cleveland, OH (US)

(72) Inventors: Eric Pearlman, Cleveland, OH (US); Sixto M. Leal, Jr., Cleveland, OH (US)

(73) Assignee: CASE WESTERN RESERVE UNIVERSITY, Cleveland, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/583,498

(22) Filed: Jan. 25, 2022

(65) Prior Publication Data

US 2022/0211820 A1 Jul. 7, 2022

Related U.S. Application Data

(63) Continuation of application No. 14/764,488, filed as application No. PCT/US2014/013606 on Jan. 29, 2014, now Pat. No. 11,229,685.

(60) Provisional application No. 61/758,003, filed on Jan. 29, 2013.

(51) Int. Cl.

| | |
|---|---|
| *A61K 38/40* | (2006.01) |
| *A61K 9/00* | (2006.01) |
| *A61K 31/69* | (2006.01) |
| *A61K 45/06* | (2006.01) |
| *A61K 31/16* | (2006.01) |
| *A61K 31/366* | (2006.01) |
| *A61K 31/4412* | (2006.01) |
| *A61K 38/16* | (2006.01) |
| *A61K 31/198* | (2006.01) |
| *A61K 31/40* | (2006.01) |
| *A61K 31/4196* | (2006.01) |
| *A61K 9/08* | (2006.01) |
| *A61K 31/22* | (2006.01) |
| *A61K 31/426* | (2006.01) |

(52) U.S. Cl.
CPC ............ *A61K 38/40* (2013.01); *A61K 9/0014* (2013.01); *A61K 9/0048* (2013.01); *A61K 9/08* (2013.01); *A61K 31/16* (2013.01); *A61K 31/198* (2013.01); *A61K 31/22* (2013.01); *A61K 31/366* (2013.01); *A61K 31/40* (2013.01); *A61K 31/4196* (2013.01); *A61K 31/426* (2013.01); *A61K 31/4412* (2013.01); *A61K 31/69* (2013.01); *A61K 38/16* (2013.01); *A61K 45/06* (2013.01)

(58) Field of Classification Search
None
See application file for complete search history.

(56) References Cited

U.S. PATENT DOCUMENTS

2009/0270496 A1 10/2009 Courchesne et al.

FOREIGN PATENT DOCUMENTS

| WO | 2008/008537 A2 | 1/2008 |
|---|---|---|
| WO | 2008/011173 A2 | 1/2008 |

OTHER PUBLICATIONS

B Ita K. Chemical penetration enhancers for transdermal drug delivery—success and challenges. Current drug delivery. Dec. 1, 2015; 12(6):645-51. (Year: 2015).*
"Fungal Keratitis" webpage from eyewiki.aao.org, Sep. 9, 2011 version accessed through the Wayback Machine (Year: 2011).*
Sinha M, Rajam M V, "Control of zoopathogenic fungi in vitro by polyamine biosynthesis inhibitors" Indian journal of experimental biology, 30 (6), p. 538-540, 1992.
Galgoczy, Laszlo Norbert, et al., "Statins as antifungal agents" World Journal of Clinical Infectious Diseases 1.1 (2011): 4-10.
Zarember, koi A. et al., "Antifungal activites of natural and synthetic iron chelators alone and in combination with azole and polyene antibiotics against aspergillus fumigatus" Antimicrobial agents and chemotherapy 53.6 (2009): 2654-2656 (Year: 2009).
Fahad, B., et al. "Aspergillus keratitis following corneal foreign body" British jounral of ophthalmology 88.6 (2004) 847-848 (Year: 2004).
Robaire, Bernard, et al.,"The Epididymis", Knobil and Neill's Physiology of Reproduction, Third Edition edited by Jimmy D. Nell, 2006, vol. 1, Chapter 22, pages, p. 1071,1112-1114.

* cited by examiner

*Primary Examiner* — Nissa M Westerberg
(74) *Attorney, Agent, or Firm* — TAROLLI, SUNDHEIM, COVELL & TUMMINO, LLP

(57) ABSTRACT

A method of treating a fungal infection in a subject includes topically administering to the subject a therapeutically effective amount of a fungal iron acquisition inhibitor to treat fungal infection in the subject.

19 Claims, 10 Drawing Sheets
Specification includes a Sequence Listing.

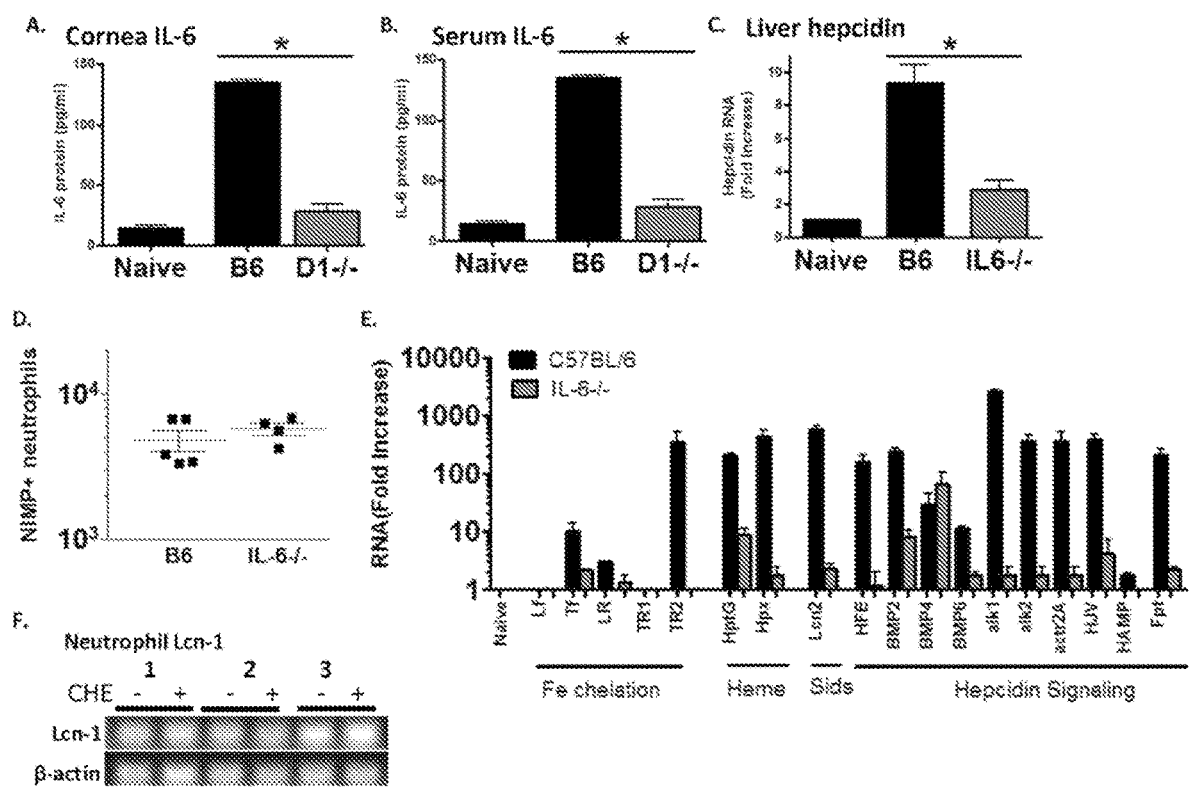
Figs. 1A-F

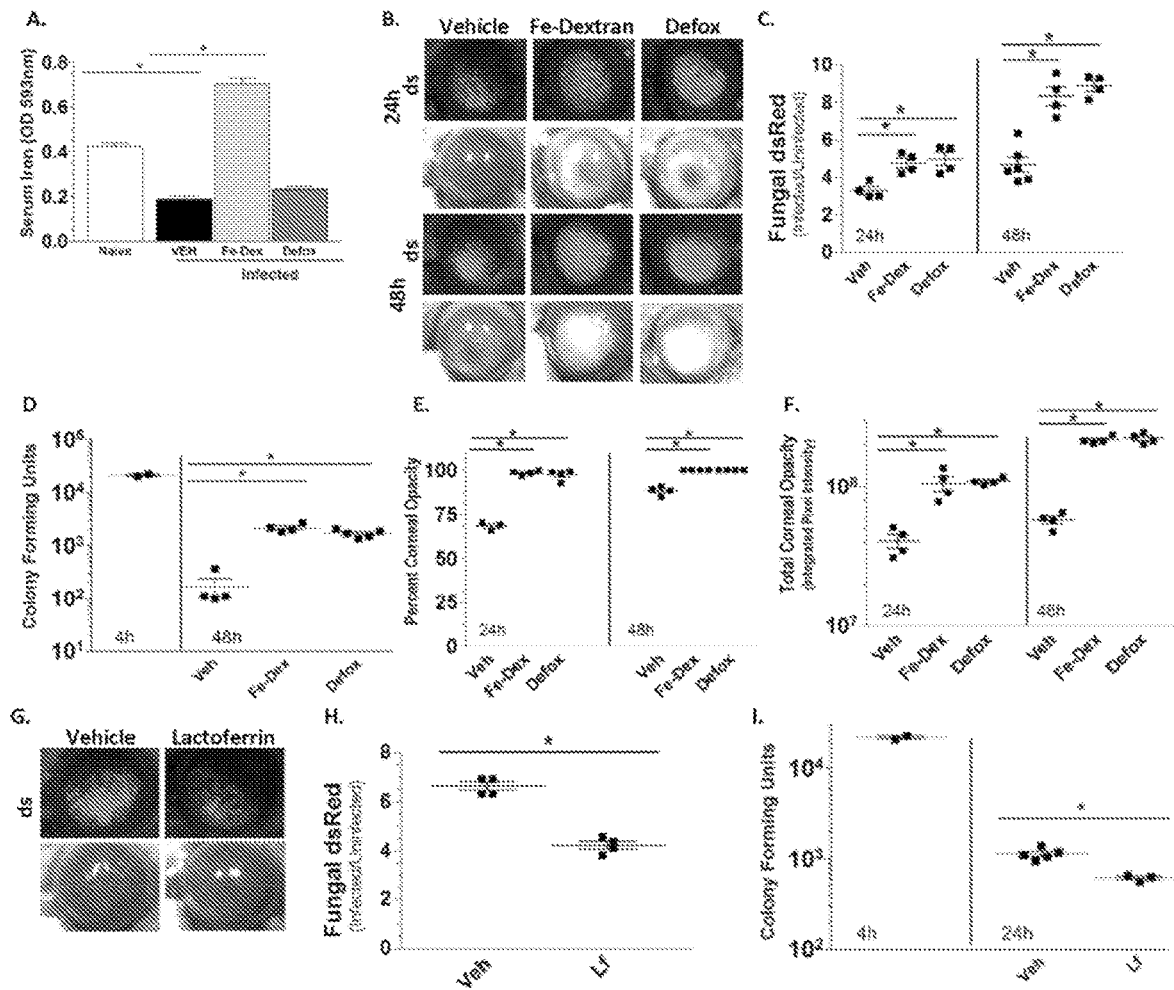
Figs. 2A-I

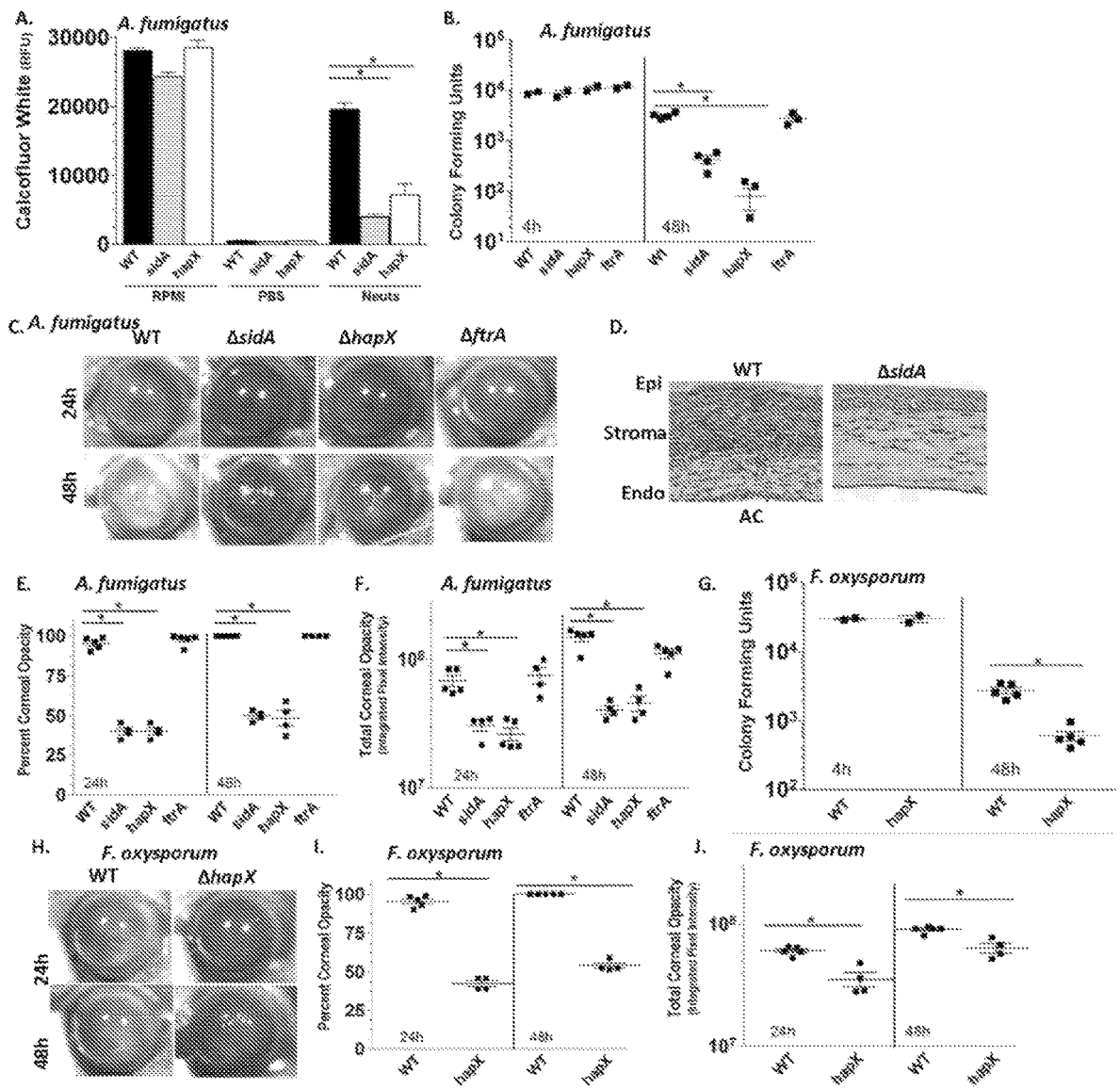
Figs. 3A-J

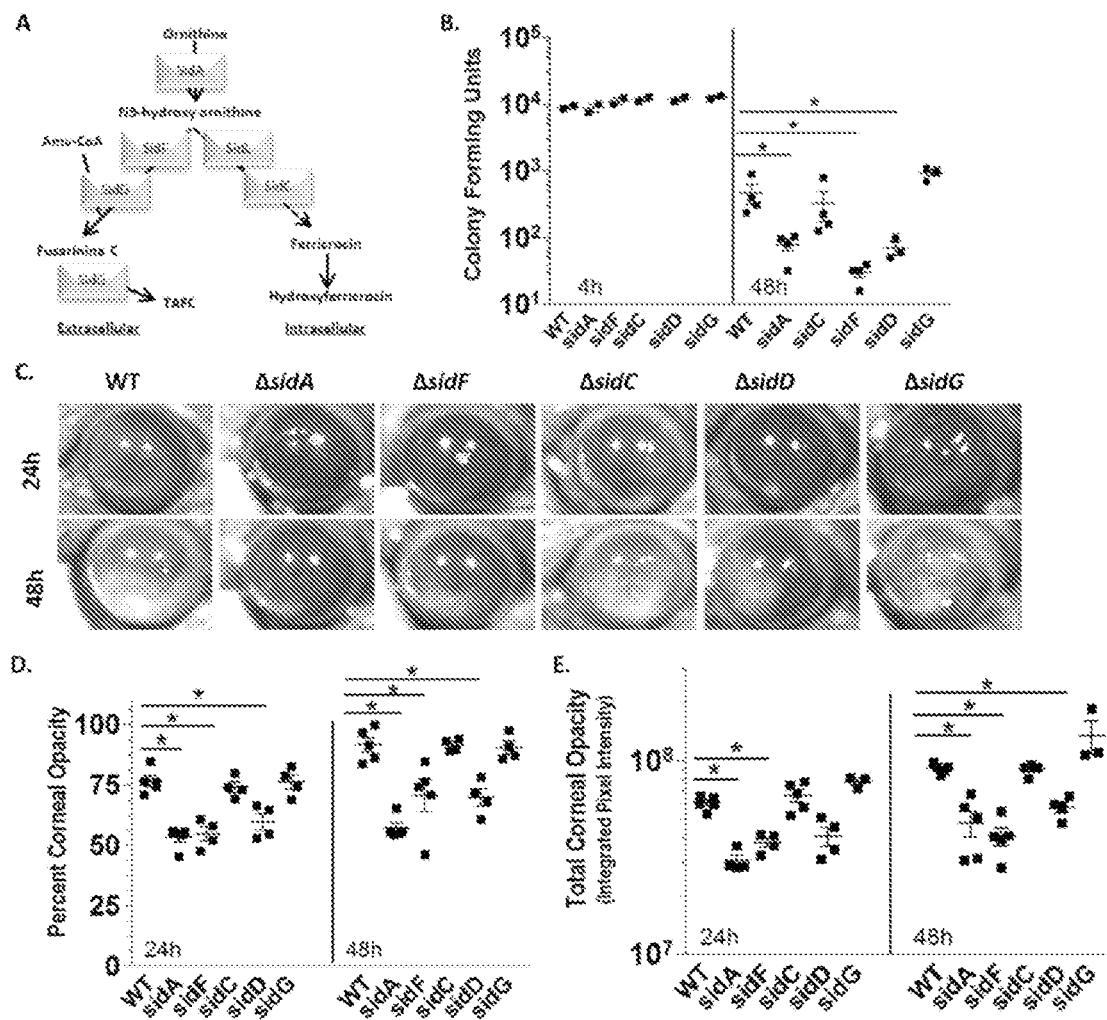
Figs. 4A-E

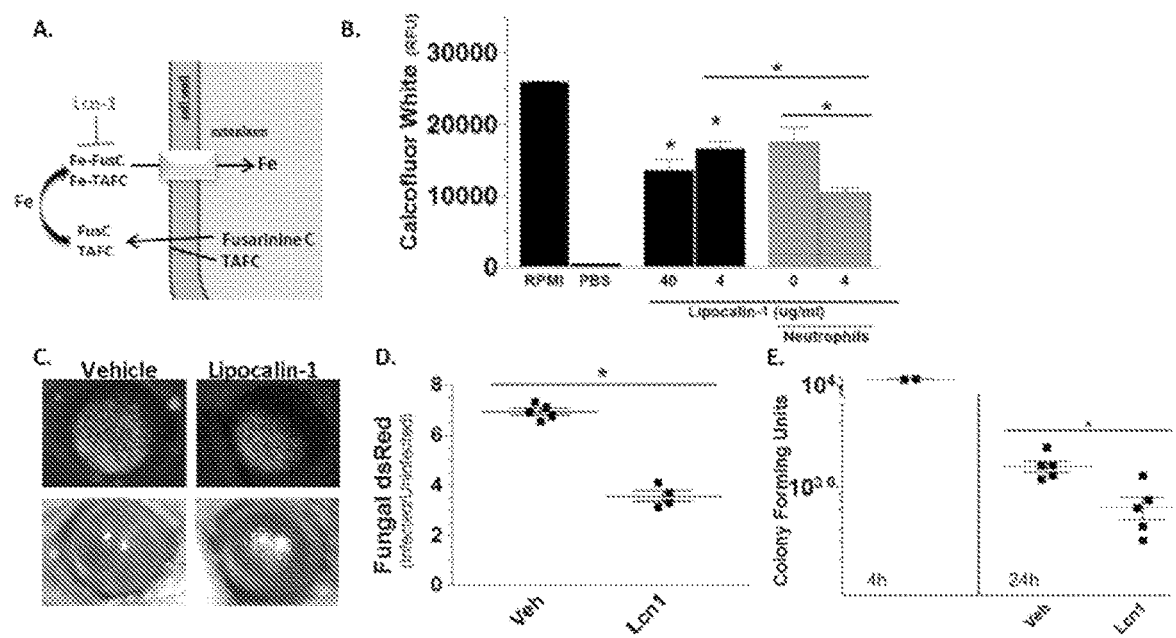
Figs. 6A-E

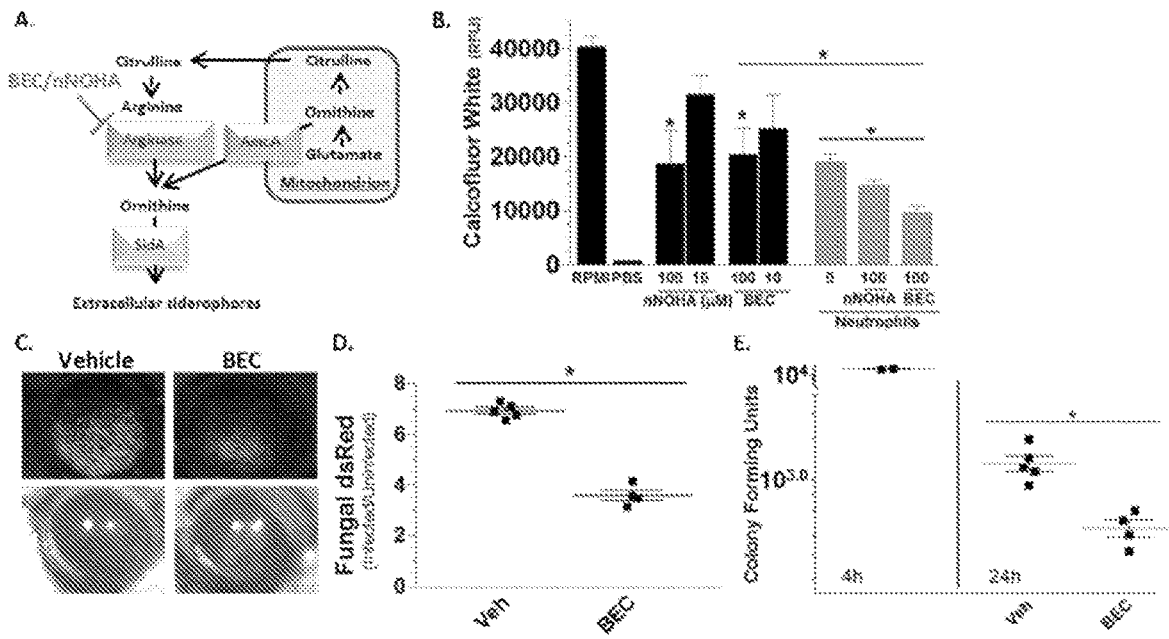
Figs. 7A-E
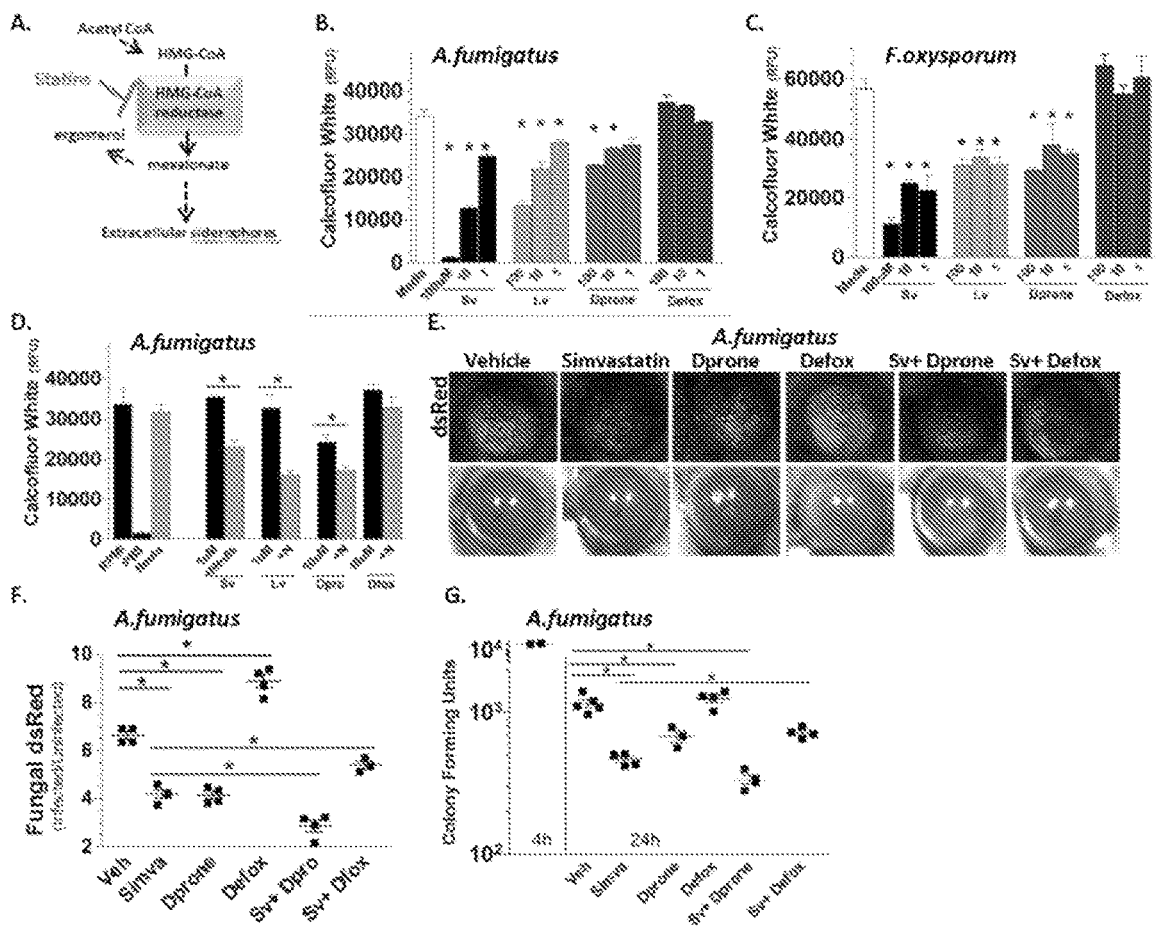
Figs. 8A-G

FUNGAL IRON ACQUISITION INHIBITORS AND USES THEREOF

RELATED APPLICATION

This application claims priority from U.S. Provisional Application No. 61/758,003, filed Jan. 29, 2013, the subject matter of which is incorporated herein by reference in its entirety.

GOVERNMENT FUNDING

This invention was made with government support under Grant No. R01EY18612 awarded by The National Institutes of Health. The United States government has certain rights to the invention.

TECHNICAL FIELD

This application relates to fungal iron acquisition inhibitors and their use in the treatment of fungal infection in a subject.

BACKGROUND

Filamentous fungi including *Aspergillus* and *Fusarium* species can cause lethal infections in immune suppressed individuals. Additionally, they infect the corneas of immunocompetent individuals and are a major cause of infectious blindness. In tropical regions of developed nations, fungal keratitis accounts for up to 35% of all corneal ulcers and is associated with contaminated contact lenses and traumatic injury with fungal-laden vegetative matter. Globally, the World Health Organization (WHO) estimates that 90% of the 1.5 to 2 million people blinded annually from corneal ulcers live in developing nations with reports of up to 65% of total corneal ulcers attributable to fungal infection. These estimates suggest a global annual incidence of fungal keratitis leading to blindness in developing nations of up to 1.2 million. In agreement with this estimate, the Fungal Research Trust, a United Kingdom-based non-profit charity estimates that in Asia and Africa alone there are approximately 1 million cases of fungal keratitis annually.

Treatment regimens for fungal keratitis are often ineffective with up to 60% of fungal keratitis cases requiring corneal transplantation. In India alone, where the incidence and prevalence of fungal keratitis are high, approximately 10,000 fungal keratitis patients annually fail medical therapy and require cornea transplants. Given the limited treatment options, there is a pressing need to develop new treatment strategies that minimize both fungal growth and host-mediated tissue damage.

SUMMARY

This application relates to methods of treating a fungal infection in a subject. The method includes administering to the subject a therapeutically effective amount of a fungal iron acquisition inhibitor to treat fungal infection in the subject.

In some aspects, the fungal iron acquisition inhibitor is selected from the group consisting of an iron chelator, a siderophore binding protein, and a siderophore biosynthesis inhibitor.

In certain aspects, the fungal iron acquisition inhibitor can include an iron chelator. The iron chelator can include lactoferrin, a 3,5-diphenyl-1,2,4-triazole derivative, and/or a salt thereof. The 3,5-diphenyl-1,2,4-triazole derivative can be selected from the group consisting of deferasirox, deferiprone, deferitrin, deferoxamine or a salt thereof. In some aspects, the iron chelator is deferiprone.

In some aspects, the fungal iron acquisition inhibitor is a siderophore biosynthesis inhibitor. The siderophore biosynthesis inhibitor can include an arginase inhibitor selected from the group consisting of (S)-(2-Boronoethyl)-L-cysteine (BEC), 2(S)-amino-6-boronohexanoic acid (ABH), $N^G$-Hydroxy-L-arginine (NOHA), $N^\omega$-Hydroxy-nor-L-arginine (nor-NOHA) and DL-alpfa-Difluoromethylornithine (DFMO). In some aspects the arginase inhibitor is BEC.

In certain aspects, the siderophore biosynthesis inhibitor includes a statin. In some aspects, the statin is selected from the group consisting of simvastatin, mevistatin, lovastatin, pravastatin, fluvastatin, atorvastatin and cerivastatin.

In some aspects, the fungal iron acquisition inhibitor is a siderophore binding protein. In certain aspects, the siderophore binding protein is lipocalin-1.

The fungal infection can include corneal, lung, skin/nail, mucosal, systemic fungal infections and combinations thereof. In some aspects, the fungal infection is selected from an *Alternaria*, *Aspergillus*, *Candida*, *Curvularia*, *Fusarium*, or *Histoplasma* fungal infection. In certain aspects, the fungal infection is a corneal fungal infection. The corneal fungal infection can include a corneal fungal infection related to *Aspergillus*, *Fusarium*, *Curvularia*, or *Alternaria*. In some aspects, the corneal fungal infection can be associated with corneal inflammation.

In some aspects, the subject does not have a fungal infection, but is at risk of developing a fungal infection. The subject may also be a neutropenic subject.

In some aspects, the fungal iron acquisition inhibitor is administered to the subject in an ophthalmic preparation. In some aspects the fungal iron acquisition inhibitor is administered to the subject in conjunction with one or more additional therapeutic agents. The one or more additional therapeutic agents can include a second fungal iron acquisition inhibitor. In certain aspects, the fungal iron acquisition inhibitor is an iron chelator and the second fungal iron acquisition inhibitor is a siderophore biosynthesis inhibitor. In certain aspects, the iron chelator is deferiprone and the siderophore biosynthesis inhibitor is a statin. The one or more additional therapeutic agents can also include an antibiotic, antiviral, and/or antifungal agent.

This application also relates to methods of treating a corneal fungal infection and/or fungal keratitis in a subject. The method includes administering to the subject a therapeutically effective amount of a fungal iron acquisition inhibitor to treat fungal infection in the subject.

In some aspects, the fungal iron acquisition inhibitor is selected from the group consisting of an iron chelator, a siderophore binding protein, and a siderophore biosynthesis inhibitor.

In certain aspects, the fungal iron acquisition inhibitor can include an iron chelator. The iron chelator can include lactoferrin, a 3,5-diphenyl-1,2,4-triazole derivative and/or a salt thereof. The 3,5-diphenyl-1,2,4-triazole derivative can be selected from the group consisting of deferasirox, deferiprone, deferitrin, deferoxamine or a salt thereof. In some aspects, the iron chelator is deferiprone.

In some aspects, the fungal iron acquisition inhibitor is a siderophore biosynthesis inhibitor. The siderophore biosynthesis inhibitor can include an arginase inhibitor selected from the group consisting of (S)-(2-Boronoethyl)-L-cysteine (BEC), 2(S)-amino-6-boronohexanoic acid (ABH), $N^G$-Hydroxy-L-arginine (NOHA), $N^\omega$-Hydroxy-nor-L-arginine (nor-NOHA) and DL-alpfa-Difluoromethylornithine (DFMO). In some aspects the arginase inhibitor is BEC.

In certain aspects, the siderophore biosynthesis inhibitor includes a statin. In some aspects, the statin is selected from the group consisting of simvastatin, mevistatin, lovastatin, pravastatin, fluvastatin, atorvastatin and cerivastatin.

In some aspects, the fungal iron acquisition inhibitor is a siderophore binding protein. In certain aspects, the siderophore binding protein is lipocalin-1.

The corneal fungal infection can include a corneal fungal infection related to *Aspergillus, Fusarium, Curvularia,* or *Alternaria*. In some aspects, the corneal fungal infection can be associated with corneal inflammation.

In some aspects, the subject does not have a corneal fungal infection, but is at risk of developing a corneal fungal infection. The subject may also be a neutropenic subject.

In some aspects, the fungal iron acquisition inhibitor is administered to the subject in an ophthalmic preparation. In some aspects the fungal iron acquisition inhibitor is administered to the subject in conjunction with one or more additional therapeutic agents. The one or more additional therapeutic agents can include a second fungal iron acquisition inhibitor. In certain aspects, the fungal iron acquisition inhibitor is an iron chelator and the second fungal iron acquisition inhibitor is a siderophore biosynthesis inhibitor. In certain aspects, the iron chelator is deferiprone and the siderophore biosynthesis inhibitor is a statin. The one or more additional therapeutic agents can also include an antibiotic, antiviral or antifungal agent.

BRIEF DESCRIPTION OF THE DRAWINGS

FIG. 1(A-F) illustrate graphs and an immunoassay showing expression of local and systemic endogenous host iron-sequestration proteins. A. Conidia from *A. fumigatus* strain dsRed were injected into the corneal stroma of C57BL/6 and Dectin-1 −/− mice, and IL-6 from either infected corneas at 10 h post-infection or B. serum at 24 h post-infection was quantified by ELISA C. At 24 h post-infection, RNA was isolated from the liver and hepcidin expression was quantified using qPCR. D. At 24 h post-infection, corneas were digested with collagenase and total neutrophils/cornea was assessed by flow cytometric analysis of cell suspensions stained with biotinylated NIMP antibody (data point represent individual corneas.) E. RNA was extracted from the corneas of infected mice and qPCR analysis was performed on host genes encoding proteins involved in iron chelation, heme or siderophore sequestratin, and hepcidin signaling. F. Neutrophils were isolated from the peripheral blood of healthy human volunteers and incubated in RPMI media or stimulated with crude hyphal extract (CHE) in RPMI media for 2 h. Subsequently, RNA was extracted, RT-PCR performed, and the product was run on a 1% agarose gel to detect Lcn-1 (data in panels A-E-are mean and SEM of 5 mice per group; data in Panel F are from three separate donors).

FIG. 2(A-I) illustrate graphs and images showing the effect of iron availability on *A. fumigatus* growth in the cornea. A. Mice were pre-treated at day-2, and day-1 with I.P. injections of iron-dextran or deferoxamine, and serum iron levels were determined 24 h post-infection (data are mean and SEM of 5 mice per group). B. Mice were infected intrastromally with conidia from *A. fumigatus* strain dsRed, and corneas were imaged at 24 h and 48 h post-infection. C. Metamorph image analyses of dsRed fluorescence. D. Colony forming units (CFU) at 4 h and 48 h post-infection. E. Metamorph image analyses was used to quantify the percent and F. total corneal opacification. G-I: Effect of lowering iron availability on fungal growth. C57BL/6 mice were infected with *A. fumigatus* dsRed conidia, and given topical lactoferrin (10.4 µg) at 0 and 6 h post infection. Corneas were examined after 24 h. G: representative images; H. image analysis of dsRed expression, and I. CFU analysis. Panels B and G show representative images, and data points in panels C-F, H and I represent individual corneas. These experiments were repeated three times with similar results.

FIG. 3(A-J) illustrate graphs and images showing susceptibility of *A. fumigatus* siderophore and iron acquisition mutants in fungal keratitis. A. *A. fumigatus* ΔsidA and ΔhapX mutants were incubated with human neutrophils, and fungal growth was quantified using calcofluor white and fluorometry. (Mean+/−SD of 5 replicate wells.) B-F: *A. fumigatus* corneal infection; G-J *F. oxysporum* corneal infection. B: CFU of C57BL/6 mice 48 h after intrastromal infection with *A. fumigatus* ΔsidA, ΔhapX, or ΔftrA mutants. C. Representative eyes showing corneal opacification at 24 h and 48 h. D. representative corneal sections stained with periodic acid-schiff and hematoxylin (PASH). E. Quantification of percent corneal opacity and F. total cornea opacity. G-J. C57BL/6 corneas were infected with *F. oxysporum* ΔhapX and the parent strain. G. CFU at 4 h and 48 h post-infection H. Representative eyes showing corneal opacification. I. Quantification of percent corneal opacity J. and total cornea opacity. Data points represent individual corneas. Similar results were found in 3 repeat experiments.

FIG. 4(A-E) illustrate a schematic drawing, plots, and images showing the role of intracellular and extracellular siderophores in *A. fumigatus* corneal infection. A. Biosynthesis of *A. fumigatus* siderophores. B-E. C57BL/6 mice were infected intrastromally with *A. fumigatus* mutant strains: ΔsidA, ΔsidC, ΔsidF, ΔsidD, or ΔsidG. B. CFU at 4 h and 48 h post-infection. C. Representative eyes showing corneal opacity. D. Quantification of percent corneal opacity and E. total cornea opacity. Similar results were found in 3 repeat experiments.

FIG. 6(A-E) illustrate a schematic drawing, images, and graphs showing the effect of exogenous lipocalin-1 in *A. fumigatus* corneal infection. A. Pathway showing Lcn-1 sequestration of fungal siderophores. B. Growth of *A. fumigatus* incubated with recombinant human Lcn-1 in the absence (black bars) or presence (gray bars) of human neutrophils determined by calcofluor white binding and quantification using fluorometry (data are mean+/−SEM of five replicate wells). C-E: C57BL/6 mice were given topical Lcn-1 (16 µg) at 0 and 6 h post-infection with *A. fumigatus* dsRed. C. Representative corneas; D. Metamorph image analysis showing fungal dsRed expression and E. CFU. Similar results were found in 3 repeat experiments.

FIG. 7(A-E) illustrate a schematic drawing, images, and graphs showing the effect of arginase inhibitors on *A. fumigatus* growth in vitro and in vivo. A. Pathway showing arginase as a target of nNOHA and BEC in siderophore biosynthesis. B. Growth of *A. fumigatus* incubated with nNOHA or BEC in the absence (black bars) or presence (gray bars) of human neutrophils by calcofluor white quantification (data are mean+/−SEM of five replicate wells). C-E: C57BL/6 mice were given topical BEC (40 µg) at 0 and 6 h post-infection with *A. fumigatus* dsRed. C. Representative corneas; D. Metamorph image analysis showing fungal dsRed expression and E. CFU. Similar results were found in 3 repeat experiments.

FIG. 8(A-G) illustrate a schematic drawing, images, and graphs showing the effect of topical simvastatin and deriprone on fungal infection. A. Statin targeting of fungal HMG-CoA reductase in siderophore biosynthesis. B, C. Effect of statins and iron chelators on growth of *A. fumigatus* and *F. oxysporum* in vitro. B. Simvastatin, lovastatin, deferiprone, or deferroxamine were added to growing cultures of *A. fumigatus* or C. *F. oxysporum* for 16 h, and hyphal growth was quantified by calcofluor white. D. Growth of *A. fumigatus* incubated with these compounds in the absence (black bars) or presence (gray bars) of human neutrophils by calcofluor white quantification (data are mean+/−SEM of five replicate wells) E. C57BL/6 mice were infected with *A. fumigatus* and at 0 and 6 h post-infection 13.4 µg of simvastatin (Sv), deferiprone (11.1 µg), deferroxamine (52.5 µg), Sv+ deferiprone, or Sv+ deferroxamine was applied topically to infected corneas and eyes were imaged at 24 h post-infection. F. Metamorph image analysis was used to quantify fungal dsRed expression and G. eyes were homogenized for CFU analysis. B-D: data are mean+/−SEM of five replicate wells; F, G: data points represent individual corneas. Similar results were found in 3 repeat experiments.

DETAILED DESCRIPTION

Figure 5A:
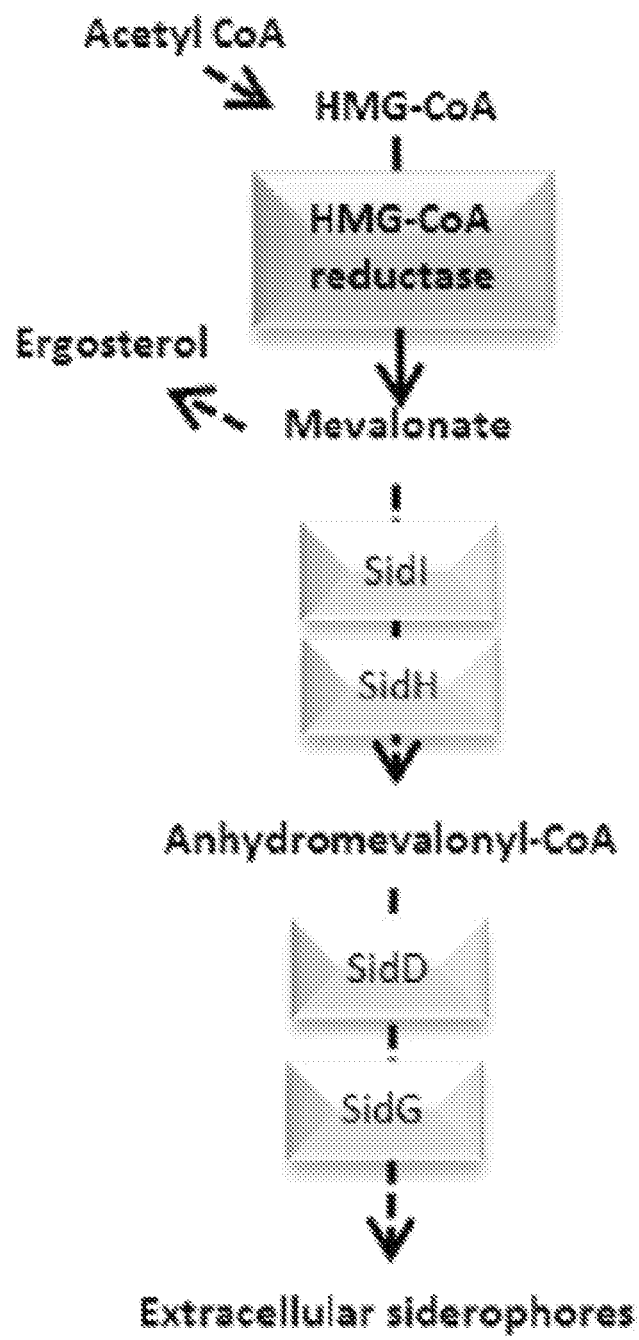
FIG. 5(A-E) illustrate a schematic drawing, plots, and images showing the role of mevalonate pathway for extracellular siderophores in *A. fumigatus* corneal infection. A. Role of SidI and SidH in siderophore biosynthesis. B-D. C57BL/6 mice were infected with *A. fumigatus* ΔsidH and ΔsidI mutant strains. B. CFU at 4 h and 48 h post-infection. C. Representative eyes showing corneal opacity D. Quantification of percent corneal opacity and E. total corneal opacity. Similar results were found in 3 repeat experiments.

The terms used in this specification generally have their ordinary meanings in the art, within the context of this invention and in the specific context where each term is used. Certain terms are discussed below, or elsewhere in the specification, to provide additional guidance to the practitioner in describing the compositions and methods of the invention and how to make and use them.

The phrase "have the formula", "having the formula" or "having the structure" is not intended to be limiting and is used in the same way that the term "comprising" is commonly used.

The term "alkyl" refers to a branched or unbranched saturated hydrocarbon group typically although not necessarily containing 1 to about 24 carbon atoms, such as methyl, ethyl, n-propyl, isopropyl, n-butyl, isobutyl, t-butyl, octyl, decyl, and the like, as well as cycloalkyl groups, such as cyclopentyl, cyclohexyl, and the like. Generally, although again not necessarily, alkyl groups herein contain 1 to about 18 carbon atoms, preferably 1 to about 12 carbon atoms. The term "lower alkyl" intends an alkyl group of 1 to 6 carbon atoms. Substituents identified as "$C_1$-$C_6$ alkyl" or "lower alkyl" can contain 1 to 3 carbon atoms, and more particularly such substituents can contain 1 or 2 carbon atoms (i.e., methyl and ethyl). "Substituted alkyl" refers to alkyl substituted with one or more substituent groups (e.g., an alkyl may optionally be substituted with one or more halogen atoms at any position along the alkyl chain), and the terms "heteroatom-containing alkyl" and "heteroalkyl" refer to alkyl in which at least one carbon atom is replaced with a heteroatom, as described in further detail infra. If not otherwise indicated, the terms "alkyl" and "lower alkyl" include linear, branched, cyclic, unsubstituted, substituted, and/or heteroatom-containing alkyl or lower alkyl, respectively.

The term "alkenyl" refers to a linear, branched or cyclic hydrocarbon group of 2 to about 24 carbon atoms containing at least one double bond, such as ethenyl, n-propenyl, isopropenyl, n-butenyl, isobutenyl, octenyl, decenyl, tetradecenyl, hexadecenyl, eicosenyl, tetracosenyl, and the like. Generally, although again not necessarily, alkenyl groups can contain 2 to about 18 carbon atoms, and more particularly 2 to 12 carbon atoms. The term "lower alkenyl" refers to an alkenyl group of 2 to 6 carbon atoms, and the specific term "cycloalkenyl" intends a cyclic alkenyl group, preferably having 5 to 8 carbon atoms. The term "substituted alkenyl" refers to alkenyl substituted with one or more substituent groups, and the terms "heteroatom-containing alkenyl" and "heteroalkenyl" refer to alkenyl in which at least one carbon atom is replaced with a heteroatom. If not otherwise indicated, the terms "alkenyl" and "lower alkenyl" include linear, branched, cyclic, unsubstituted, substituted, and/or heteroatom-containing alkenyl and lower alkenyl, respectively.

The term "alkynyl" refers to a linear or branched hydrocarbon group of 2 to 24 carbon atoms containing at least one triple bond, such as ethynyl, n-propynyl, and the like. Generally, although again not necessarily, alkynyl groups can contain 2 to about 18 carbon atoms, and more particularly can contain 2 to 12 carbon atoms. The term "lower alkynyl" intends an alkynyl group of 2 to 6 carbon atoms. The term "substituted alkynyl" refers to alkynyl substituted with one or more substituent groups, and the terms "heteroatom-containing alkynyl" and "heteroalkynyl" refer to alkynyl in which at least one carbon atom is replaced with a heteroatom. If not otherwise indicated, the terms "alkynyl" and "lower alkynyl" include linear, branched, unsubstituted, substituted, and/or heteroatom-containing alkynyl and lower alkynyl, respectively.

The term "alkoxy" refers to an alkyl group bound through a single, terminal ether linkage; that is, an "alkoxy" group may be represented as —O-alkyl where alkyl is as defined above. A "lower alkoxy" group intends an alkoxy group containing 1 to 6 carbon atoms, and includes, for example, methoxy, ethoxy, n-propoxy, isopropoxy, t-butyloxy, etc. Preferred substituents identified as "$C_1$-$C_6$ alkoxy" or "lower alkoxy" herein contain 1 to 3 carbon atoms, and particularly preferred such substituents contain 1 or 2 carbon atoms (i.e., methoxy and ethoxy).

The term "aryl" refers to an aromatic substituent containing a single aromatic ring or multiple aromatic rings that are fused together, directly linked, or indirectly linked (such that the different aromatic rings are bound to a common group such as a methylene or ethylene moiety). Aryl groups can contain 5 to 20 carbon atoms, and particularly preferred aryl groups can contain 5 to 14 carbon atoms. Exemplary aryl groups contain one aromatic ring or two fused or linked aromatic rings, e.g., phenyl, naphthyl, biphenyl, diphenylether, diphenylamine, benzophenone, and the like. "Substituted aryl" refers to an aryl moiety substituted with one or more substituent groups, and the terms "heteroatom-containing aryl" and "heteroaryl" refer to aryl substituent, in which at least one carbon atom is replaced with a heteroatom, as will be described in further detail infra. If not otherwise indicated, the term "aryl" includes unsubstituted, substituted, and/or heteroatom-containing aromatic substituents.

The term "aryloxy" as used herein refers to an aryl group bound through a single, terminal ether linkage, wherein "aryl" is as defined above. An "aryloxy" group may be represented as —O-aryl where aryl is as defined above. Preferred aryloxy groups contain 5 to 20 carbon atoms, and particularly preferred aryloxy groups contain 5 to 14 carbon atoms. Examples of aryloxy groups include, without limitation, phenoxy, o-halo-phenoxy, m-halo-phenoxy, p-halo-phenoxy, o-methoxy-phenoxy, m-methoxy-phenoxy, p-methoxy-phenoxy, 2,4-dimethoxy-phenoxy, 3,4,5-trimethoxy-phenoxy, and the like.

The term "alkaryl" refers to an aryl group with an alkyl substituent, and the term "aralkyl" refers to an alkyl group with an aryl substituent, wherein "aryl" and "alkyl" are as defined above. Exemplary aralkyl groups contain 6 to 24 carbon atoms, and particularly preferred aralkyl groups contain 6 to 16 carbon atoms. Examples of aralkyl groups include, without limitation, benzyl, 2-phenyl-ethyl, 3-phenyl-propyl, 4-phenyl-butyl, 5-phenyl-pentyl, 4-phenylcyclohexyl, 4-benzylcyclohexyl, 4-phenylcyclohexylmethyl, 4-benzylcyclohexylmethyl, and the like. Alkaryl groups include, for example, p-methylphenyl, 2,4-dimethylphenyl, p cyclohexylphenyl, 2,7-dimethylnaphthyl, 7-cyclooctylnaphthyl, 3-ethyl-cyclopenta-1,4-diene, and the like.

The term "cyclic" refers to alicyclic or aromatic substituents that may or may not be substituted and/or heteroatom containing, and that may be monocyclic, bicyclic, or polycyclic.

The terms "halo" and "halogen" are used in the conventional sense to refer to a chloro, bromo, fluoro or iodo substituent.

The term "heteroatom-containing" as in a "heteroatom-containing alkyl group" (also termed a "heteroalkyl" group) or a "heteroatom-containing aryl group" (also termed a "heteroaryl" group) refers to a molecule, linkage or substituent in which one or more carbon atoms are replaced with an atom other than carbon, e.g., nitrogen, oxygen, sulfur, phosphorus or silicon, typically nitrogen, oxygen or sulfur. Similarly, the term "heteroalkyl" refers to an alkyl substituent that is heteroatom-containing, the term "heterocyclic" refers to a cyclic substituent that is heteroatom-containing, the terms "heteroaryl" and heteroaromatic" respectively refer to "aryl" and "aromatic" substituents that are heteroatom-containing, and the like. Examples of heteroalkyl groups include alkoxyaryl, alkylsulfanyl-substituted alkyl, N-alkylated amino alkyl, and the like. Examples of heteroaryl substituents include pyrrolyl, pyrrolidinyl, pyridinyl, quinolinyl, indolyl, pyrimidinyl, imidazolyl, 1,2,4-triazolyl, tetrazolyl, etc., and examples of heteroatom-containing alicyclic groups are pyrrolidino, morpholino, piperazino, piperidino, etc.

By "substituted" as in "substituted alkyl," "substituted aryl," and the like, as alluded to in some of the aforementioned definitions, is meant that in the alkyl, aryl, or other moiety, at least one hydrogen atom bound to a carbon (or other) atom is replaced with one or more non-hydrogen substituents. In addition, the aforementioned functional groups may, if a particular group permits, be further substituted with one or more additional functional groups or with one or more hydrocarbyl moieties such as those specifically enumerated above. Analogously, the above-mentioned hydrocarbyl moieties may be further substituted with one or more functional groups or additional hydrocarbyl moieties such as those specifically enumerated.

When the term "substituted" appears prior to a list of possible substituted groups, it is intended that the term apply to every member of that group. For example, the phrase "substituted alkyl, alkenyl, and aryl" is to be interpreted as "substituted alkyl, substituted alkenyl, and substituted aryl." Analogously, when the term "heteroatom-containing" appears prior to a list of possible heteroatom-containing groups, it is intended that the term apply to every member of that group. For example, the phrase "heteroatom-containing alkyl, alkenyl, and aryl" is to be interpreted as "heteroatom-containing alkyl, substituted alkenyl, and substituted aryl."

"Optional" or "optionally" means that the subsequently described circumstance may or may not occur, so that the description includes instances where the circumstance occurs and instances where it does not. For example, the phrase "optionally substituted" means that a non-hydrogen substituent may or may not be present on a given atom, and, thus, the description includes structures wherein a non-hydrogen substituent is present and structures wherein a non-hydrogen substituent is not present.

As used herein, the term "fungal iron acquisition inhibitor" refers to an agent, such as a small molecule, polypeptide, or polynucleotide that is capable of substantially reducing, inhibiting, blocking, and/or mitigating the acquisition of iron in a fungus or fungal cell. In some aspects, a fungal iron acquisition inhibitor can include an agent that significantly increases host iron sequestration. In some aspects, a fungal iron acquisition inhibitor can include an agent that inhibits an iron acquisition mediator in a fungal cell. Examples of fungal iron acquisition inhibitors can include iron chelators, siderophore biosynthesis inhibitors and siderophore binding proteins.

The terms "chelator" or "metal chelator" refer to any substance that is able to remove a metal ion from a solution system by forming a new complex ion that has different chemical properties than those of the original metal ion. The term is further intended to encompass substances that are capable of chelating metal ions, specifically divalent metals.

The term "effective amount" refers to a dosage of a therapeutic agent administered alone or in conjunction with any additional therapeutic agents that are effective and/or sufficient to provide treatment of fungal infection and/or a disease or disorder associated with fungal infection. The effective amount can vary depending on the subject, the disease being treated, and the treatment being effected.

The term "metal ions" is intended to include any metal ion that is bioavailable, i.e., any metal ion involved in a biochemical reaction or pathway, or any metal ion that is available in the fluid, tissue, or bone of a subject.

The terms "pharmaceutically or pharmacologically acceptable" refer to molecular entities and compositions that do not produce an adverse, allergic or other untoward reaction when administered to an animal, or a human, as appropriate. Veterinary uses are equally included within the invention and "pharmaceutically acceptable" formulations include formulations for both clinical and/or veterinary use.

The terms "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. For human administration, preparations should meet sterility, pyrogenicity, general safety and purity standards as required by FDA Office of Biologics standards. Supplementary active ingredients can also be incorporated into the compositions.

The term "pharmaceutically acceptable salt" includes salts of compounds derived from the combination of the compound and an organic or inorganic acid or base. In some embodiments a pharmaceutically acceptable salt can include hydrohalide, acetate, sulfonate, tosylate, or a phosphate.

The term "subject" refers to any warm-blooded organism including, but not limited to, human beings, pigs, rats, mice, dogs, goats, sheep, horses, monkeys, apes, rabbits, cattle, etc.

The terms "treatment," "treating," or "treat" refers to any specific method or procedure used for the cure of, inhibition of, reduction of, elimination of, or the amelioration of a disease or pathological condition (e.g., fungal infection) including, for example, preventing fungal infection from developing, inhibiting fungal infection development, arresting development of clinical symptoms associated with fungal infection, and/or relieving the symptoms associated with fungal infection.

The term "therapeutically effective amount" refers to that amount of a therapeutic agent topically administered alone and/or in combination with additional therapeutic agents that results in amelioration of symptoms associated with fungal infection and/or a disease or disorder associated with fungal infection and/or results in a therapeutically relevant effect. The therapeutically effective amount can vary depending on the subject, the disease being treated, and the treatment being effected. By way of example, a "therapeutically effective amount" may be understood as an amount of an antifungal agent inhibitor required to reduce the fungal mass and/or fungal growth rate of a fungal infection in a subject.

The term "thioredoxin protein inhibitor" refers to an agent, such as a small molecule, polypeptide, polynucleotide, that is capable of substantially reducing, inhibiting, blocking, and/or mitigating the activation of thioredoxin protein in a fungal cell. In one example, a thioredoxin protein inhibitor binds to the active site of the thioredoxin protein, thereby inhibiting its ability to partake in redox reactions and quench cytoplasmic reactive oxygen species (ROS).

The terms "treatment," "treating," or "treat" refers to any specific method or procedure used for the cure of, inhibition of, reduction of, elimination of, or the amelioration of a disease or pathological condition (e.g. fungal infection) including, for example, preventing fungal infection from developing, inhibiting fungal infection development, arresting development of clinical symptoms associated with fungal infection, and/or relieving the symptoms associated with fungal infection.

As used herein, "unit dosage" formulations are those containing a dose or sub-dose of the administered ingredient adapted for a particular timed delivery. For example, "unit dosage" formulations are those containing a daily dose or unit or daily sub-dose or a weekly dose or unit or weekly sub-dose and the like.

The term "zinc chelator" refers to any substance that is able to chelate a zinc ($Zn^{2+}$) ion and thus deplete zinc from aqueous environments.

Embodiments described herein relate to methods of treating, reducing, inhibiting, and/or mitigating a fungal infection in a subject by topically administering a therapeutically effective amount of one or more fungal iron acquisition inhibitor(s) to the subject. It was found that fungal iron acquisition and/or siderophore biosynthesis is an essential mediator of fungal growth during infection. Targeting fungal iron acquisition and/or siderophore biosynthesis by topical application of iron chelators, arginase inhibitors and/or statins can inhibit fungal growth and reduce fungal infection by increasing susceptibility of a fungal cell to oxidative stress.

In some embodiments, a fungal iron acquisition inhibitor for use in a method described herein can include any agent or therapeutic agent that when topically or locally administered to a subject having a fungal infection is capable of substantially reducing, inhibiting, blocking, and/or mitigating the acquisition of iron in a fungal cell and thus inhibit the fungal cell's ability to minimize cellular damage from both exogenous and endogenous reactive oxygen species (ROS) sources and reduce the fungal cell's growth rate. In certain embodiments, a fungal iron acquisition inhibitor employed in the method described herein is effective in the treatment of fungal infection by enhancing fungal cell susceptibility to endogenous neutrophils induced fungal cell death. In other embodiments, a fungal iron acquisition inhibitor is effective in killing and/or reducing the growth rate of fungal cells in a subject in the absence of neutrophils.

In certain embodiments, the fungal iron acquisition inhibitor can include an agent capable of inhibiting the ability of fungal cells to acquire iron in a subject by sequestering host free (or bio-available) iron from the fungal cell microenvironment. In some embodiments an agent that sequesters host free iron can be an iron chelator. The term "iron chelator", or "iron chelating compound", refers to a compound that binds iron between two or more separate binding sites so as to form a chelate ring or rings. An iron chelating compound bound or complexed with iron is referred to herein as an iron chelate.

An iron chelating compound can be bidentate (or didentate), which binds iron using two separate binding sites. Iron chelating compounds also can be tridentate, tetradentate or higher order multidentate iron chelation compounds binding iron with three, four or more separate binding sites, respectively. Iron chelating compounds can include chelation compounds that can bind to all oxidation states of iron including, for example, iron (-II) state, iron (-I) state, iron (0) state, iron (I) state, iron (II) state (ferrous), iron (III) state (ferric), iron (IV) state (ferryl) and/or iron (V). Iron chelation therapy refers to the use of an iron chelator to bind with iron in vivo to form an iron chelate so that the iron loses adverse physiological activity. Alternatively, chelated iron becomes unavailable to the infectious organism.

One example of an iron chelator that can be used as a fungal iron acquisition inhibitor in the methods described herein can include the iron chelating protein lactoferrin. In an exemplary embodiment, an *A. fumigatus* infected cornea can be treated by topically administering lactoferrin (10.4 µg in 8 µl) at 0 h and 6 h post infection to significantly decrease fungal mass and CFU at 24 h post-infection compared to untreated infected corneas as shown in FIG. 2 G-I.

Another example of an iron chelator that can be used in the methods described herein can include a 3,5-diphenyl-1, 2,4-triazole derivative or a salt thereof, e.g., deferasirox, deferiprone, deferitrin, and deferoxamine. In certain embodiments, the iron chelator can be deferiprone. For example, as shown in FIG. 8 the iron chelator deferiprone sensitizes fungi to human neutrophils and blocks fungal infection in vivo in mice. The term "deferiprone," as it is used herein is intended to mean an iron chelating compound having the structure 1,2 dimethyl-3-hydroxypyrid-4-1. Deferiprone (Def) also is known in the art as L1, CP20, Ferriprox, or Kelfer. Deferiprone is a member of the α-ketohydroxypyridine class of iron chelators and is commercially available from, for example, Apotex, Inc. (Weston, Ontario, Canada).

Other iron chelating compounds can also be used as a fungal iron acquisition inhibitor in the methods described herein. Such other iron chelating compounds can include naturally occurring siderophores and xenosiderophores as well as non-naturally occurring siderophores and xenosiderophores.

The term "siderophore," as it is used herein is intended to mean an iron chelator that facilitates iron gathering by an organism. For example, under conditions of iron starvation, many fungi synthesize siderophores that function in iron gathering through iron binding and uptake. Siderophores are generally low molecular weight compounds (e.g., less than about 2,000 MW) and can exhibit either or both cellular uptake and/or iron storage functions. Siderophores are synthesized by the utilizing organism. As compared to the term "iron chelator," which is generally used without reference to organism or species specificity, the term "siderophore" as it is used herein refers to an iron chelator in context with, or relative to, the siderophore-producing and utilizing organism or species. Accordingly, although iron chelating siderophores bind and decrease iron levels from the extracellular environment, because they facilitate iron uptake and use by a pathogen they have diminished therapeutic value when used for iron chelation therapy targeting a condition caused by the siderophore-producing organism.

The term "xenosiderophore," as it is used herein is intended to mean a siderophore not produced by the utilizing fungus or organism. The term "xenosiderophore" refers to an iron chelator in context with, or relative to, the xenosiderophore utilizing organism or species. Similar to siderophores, xenosiderophores exhibit therapeutic value when used for iron chelation therapy that targets a condition caused by a non-utilizing organism. Siderophore and xenosiderophore synthesis and use can be found described in, for example, Howard, D. H., FEMS Immunology and Medical Microbiology 40:95-100 (2004).

Examples of siderophores and xenosiderophores include hydroxamates and polycarboxylates. Hydroxamates contain an N-δ-hydroxyornithine moiety and are generally categorized into four exemplary families. One category includes rhodotorulic acid, which is the diketopiperazine of N-δ-acetyl-L-N δ-hydroxyornithine. Included within this category are derivatives such as dihydroxamate named dimerum acid. A second category includes the coprogens, which contain an N-δ-acyl-N-δ-hydroxy-L-ornithine moiety. Coprogens also can be considered trihydroxamate derivatives of rhodotorulic acid with a linear structure. A third category includes the ferrichromes, which consist of cyclic peptides containing a tripeptide of N-δ-acyl-N-δ-hydroxyornithine and combinations of glycine, serine or alanine. The fourth exemplary category includes the fusarinines, also called fusigens, which can be either linear or cyclic hydroxamates. Fusarinine is a compound characterized by N acylation of N-hydroxyornithine by anhydromevalonic acid.

Polycarboxylates consist of a citric acid-containing polycarboxylate called rhizoferrin. The molecule contains two citric acid units linked to diaminobutane. Rhizoferrin is widely distributed among the members of the phylum Zygomycota, having been observed in the order Mucorales and in the order Entomophthorales. Other categories of siderophores useful as iron chelating compounds in a method of the invention include, for example, the phenolate-catecholate class of siderophores, hernin, and β-ketoaldehyde phytotoxins.

In other embodiments, the fungal iron acquisition inhibitor can be an agent capable of inhibiting the fungal siderophore biosynthesis of a pathogenic fungal cell in a subject (i.e., a fungal siderophore biosynthesis inhibitor). Pathogenic fungal siderophore biosynthesis has been identified as an essential mediator of fungal growth during infection. For example, siderophore production by filamentous fungi requires the precursor amino acid ornithine, which is produced in the mitochondria and exported to the cytoplasm through the ornithine transporter AMcA or produced directly in the cytosol from arginine by the enzyme arginase. It is contemplated that agents capable of targeting fungal arginase (i.e., arginase inhibitors), which mediates ornithine and therefore siderophore biosynthesis, can be used as fungal iron acquisition inhibitors in a method described herein by facilitating neutrophil killing of fungal cells and inhibiting fungal growth during infection.

In one example, as illustrated in FIG. 7C-E, *A. fumigatus* infected mice treated with the arginase inhibitor, (S)-(2-Boronoethyl)-L-cysteine (BEC), (40 μg in 8 μl) had significantly lower fungal mass and CFU at 24 h post-infection compared to control infected mice. Furthermore, it was shown that there were no apparent ill effects on the cornea following BEC treatment. Therefore, in some embodiments, a fungal iron acquisition inhibitor can include an arginase inhibitor. In certain embodiments, the arginase inhibitor can be BEC.

Additional arginase inhibitors can include but are not limited to 2(S)-amino-6-boronohexanoic acid (ABH), $N^G$-Hydroxy-L-arginine (NOHA), $N^\omega$-Hydroxy-nor-L-arginine (nor-NOHA) and DL-alpfa-Difluoromethylornithine (DFMO also called eflornithine).

In other embodiments, a fungal siderophore biosynthesis inhibitor can include a statin drug. As discussed in the example below, statins target the enzyme HMG-CoA reductase, which is required for fungal siderophore biosynthesis. As used herein, the term "statin" or "statin drug" can refer to any compound or agent capable of substantially inhibiting HMG Co-A (3-hydroxy methylglutaryl coenzyme A) reductase.

Statins that can be used for administration, or co-administration with other agents described herein include, but are not limited to, simvastatin (U.S. Pat. No. 4,444,784), mevistatin, lovastatin (U.S. Pat. No. 4,231,938), pravastatin sodium (U.S. Pat. No. 4,346,227), fluvastatin (U.S. Pat. No. 4,739,073), atorvastatin (U.S. Pat. No. 5,273,995), cerivastatin, and numerous others described in U.S. Pat. Nos. 5,622,985, 5,135,935, 5,356,896, 4,920,109, 5,286,895, 5,262,435, 5,260,332, 5,317,031, 5,283,256, 5,256,689, 5,182,298, 5,369,125, 5,302,604, 5,166,171, 5,202,327, 5,276,021, 5,196,440, 5,091,386, 5,091,378, 4,904,646, 5,385,932, 5,250,435, 5,132,312, 5,130,306, 5,116,870, 5,112,857, 5,102,911, 5,098,931, 5,081,136, 5,025,000, 5,021,453, 5,017,716, 5,001,144, 5,001,128, 4,997,837, 4,996,234, 4,994,494, 4,992,429, 4,970,231, 4,968,693, 4,963,538, 4,957,940, 4,950,675, 4,946,864, 4,946,860 U.S. Pat. Nos. 4,940,800, 4,940,727, 4,939,143, 4,929,620, 4,923,861, 4,906,657, 4,906,624 and 4,897,402, the disclosures of which patents are incorporated herein by reference in their entirety.

In another example, incubation of *A. fumigatus* and *Fusarium oxysporum* in the presence of the statins simvastatin and lovastatin resulted in significantly less fungal cell growth in vitro (FIG. 8B-D). In addition, topical administration of 13.4 μg of simvastatin at 0 and 6 h post-infection inhibited fungal growth in *A. fumigatus* infected mice corneas (FIG. 8E). Therefore, in certain embodiments, a statin for use as a fungal iron acquisition inhibitor in a method described herein can include simvastatin and/or lovastatin.

In other embodiments, a fungal iron acquisition inhibitor can include a siderophore-binding agent. A siderophore-binding agent described herein can include any agent (e.g., a protein) that is capable of binding to a pathogenic fungal siderophore and substantially reducing, inhibiting, blocking, and/or mitigating the functional activity of the pathogenic fungal siderophore. An example of a siderophore-binding protein is lipocalin-1 (Lcn-1). Lcn-1 is produced by humans and binds to a wide range of bacterial and fungal hydroxymate-type siderophores. Therefore, a fungal siderophore binding protein for use in a method described herein can include Lcn-1.

In another example, 4 µg/ml or 40 µg/ml Lcn-1 significantly decreased fungal growth (*A. fumigatus*) and further decreased fungal growth in the presence of neutrophils. As shown in FIGS. 6C-E, mice treated with topical Lcn-1 (16 µg/80) at 0 h and 6 h after infection had significantly less fungal mass and CFU compared with infected mice in the absence of exogenous Lcn-1 indicating that sequestering fungal siderophores with topical Lcn-1 inhibits fungal growth in vivo.

In some embodiments, the fungal iron acquisition inhibitors can be administered to subjects, such as mammals, afflicted with a fungal infection. Non-limiting examples of fungal infections treated using a method described herein include corneal, lung, skin/nail, mucosal, and systemic fungal infections.

In other embodiments, the fungal iron acquisition inhibitors can be used to treat corneal fungal infections and related inflammation. For example, in certain embodiments, the fungal iron acquisition inhibitors may be used to treat fungal keratitis. The fungal keratitis may be related to fungal genera including, for example, *Fusarium, Penicillium, Aspergillus, Cephalosporium (Acremonium), Curvularia, Alternaria, Trichophyton, Microsporum, Epidermophyton, Scopulariopsis*, and *Candida*.

In particular embodiments, the fungal iron acquisition inhibitors may be used to treat: lung fungal infections related to fungal genera including for example, *Aspergillus* and *Histoplasma*; skin/nail fungal infections (e.g., Athlete's Foot) related to fungal general including for example, *Microsporum, Epidermophyton* and *Trichophyton*; mucosal fungal infections related to fungal genera including for example, *Candida*; and systemic fungal infections related to fungal genera including for example, *Candida* and *Aspergillus*.

The fungal iron acquisition inhibitors may also be used in the treatment and prevention of a nosocomial fungal infection (i.e., hospital-acquired fungal infections). In some embodiments, a fungal iron acquisition inhibitor can be administered to a subject who has undergone a medical intervention (e.g., a surgical intervention). In an alternative embodiment, a fungal iron acquisition inhibitor can be administered to a subject prior to the subject undergoing a medical intervention. Additionally, a fungal iron acquisition inhibitor can be administered to a subject both prior to and after the subject has undergone a medical intervention.

In other embodiments, subjects who do not have, but are at risk of developing a fungal infection can be treated with the fungal iron acquisition inhibitors. In such subjects, the treatment can inhibit or prevent the development of fungal infection in the subject.

For example, the methods can be administered to neutropenic subjects. Neutropenic subjects can have neutropenia related to current or prior immunosuppressive therapy, an infection (e.g., AIDS) or an otherwise dysfunctional immune system. Neutropenic subjects are predisposed to the development of invasive fungal infections, most commonly including *Candida* species and *Aspergillus* species, and, on occasion, *Fusarium, Trichosporon* and Dreschlera. Cryptoccocus infection is also common in patients on immunosuppressive agents.

The fungal iron acquisition inhibitor used in methods can be administered to the subject to treat fungal infection using standard methods including, for example, ophthalmic, topical, parenteral, subcutaneous, intravenous, intraarticular, intrathecal, intramuscular, intraperitoneal, intradermal injections, or by transdermal, buccal, oromucosal, oral routes or via inhalation. The particular approach and dosage used for a particular subject depends on several factors including, for example, the general health, weight, and age of the subject. Based on factors such as these, a medical practitioner can select an appropriate approach to treatment.

Treatment according to the methods can be altered, stopped, or re-initiated in a subject depending on the status of fungal infection (e.g., corneal fungal infection). Treatment can be carried out as intervals determined to be appropriate by those skilled in the art. For example, the administration can be carried out 1, 2, 3, or 4 times a day. In another aspect, a fungal iron acquisition inhibitor can be administered after induction of the inflammatory response/exposure to human neutrophils has occurred.

The methods can include administering to the subject a therapeutically effective amount of a fungal iron acquisition inhibitor. Determination of a therapeutically effective amount is within the capability of those skilled in the art. The exact formulation, route of administration, and dosage can be chosen by the individual physician in view of the subject's condition.

In particular embodiments, the therapeutically effective amount is equal to, or greater than, the amount of a particular agent sufficient to cause systemic side effects and/or an increased risk of death when administered to a subject systemically but that does not cause systemic side effects or an increased risk of death when administered topically (e.g., ophthalmically).

Formulation of pharmaceutical compounds for use in the modes of administration noted above (and others) are described, for example, in *Remington's Pharmaceutical Sciences* (18$^{th}$ edition), ed. A. Gennaro, 1990, Mack Publishing Company, Easton, Pa. (also see, e.g., M. J. Rathbone, ed., Oral Mucosal Drug Delivery, Drugs and the Pharmaceutical Sciences Series, Marcel Dekker, Inc., N.Y., U.S.A., 1996; M. J. Rathbone et al., eds., Modified-Release Drug Delivery Technology, Drugs and the Pharmaceutical Sciences Series, Marcel Dekker, Inc., N.Y., U.S.A., 2003; Ghosh et al., eds., Drug Delivery to the Oral Cavity, Drugs and the Pharmaceutical Sciences Series, Marcel Dekker, Inc., N.Y. U.S.A., 1999.

In some embodiments, the fungal iron acquisition inhibitor can be provided in ophthalmic preparation that can be administered to the subject's eye for the treatment of a corneal fungal infection. The ophthalmic preparation can include a fungal iron acquisition inhibitor in a pharmaceutically acceptable solution, suspension, or ointment. Some variations in concentration can occur, depending on the particular fungal iron acquisition inhibitor employed, the condition of the subject to be treated and the like, and the person responsible for treatment can determine the most suitable concentration for the individual subject. In one particular embodiment, an ophthalmic preparation for the treatment of a corneal fungal infection includes the fungal iron acquisition inhibitor deferiprone (10 mM) suspended in a commercial eye drop formulation (Alcon Laboratories). The ophthalmic preparation can be in the form of a sterile aqueous solution containing, if desired, additional ingredients, for example, preservatives, buffers, tonicity agents, antioxidants, stabilizers, nonionic wetting or clarifying agents, and viscosity increasing agents.

Examples of preservatives for use in such a solution include benzalkonium chloride, benzethonium chloride, chlorobutanol, thimerosal and the like. Examples of buffers include boric acid, sodium and potassium bicarbonate, sodium and potassium borates, sodium and potassium carbonate, sodium acetate, and sodium biphosphate, in amounts sufficient to maintain the pH at between about pH 6 and about pH 8, and for example, between about pH 7 and about pH 7.5. Examples of tonicity agents are dextran 40, dextran 70, dextrose, glycerin, potassium chloride, propylene glycol, and sodium chloride.

Examples of antioxidants and stabilizers include sodium bisulfite, sodium metabisulfite, sodium thiosulfite, and thiourea. Examples of wetting and clarifying agents include polysorbate 80, polysorbate 20, poloxamer 282 and tyloxapol. Examples of viscosity-increasing agents include gelatin, glycerin, hydroxyethylcellulose, hydroxymethylpropylcellulose, lanolin, methylcellulose, petrolatum, polyethylene glycol, polyvinyl alcohol, polyvinylpyrrolidone, and carboxymethylcellulose. The ophthalmic preparation will be administered topically to the eye of the subject in need of treatment by conventional methods, for example, in the form of drops or by bathing the eye in the ophthalmic solution.

The fungal iron acquisition inhibitors can also be formulated for topical administration through the skin. "Topical delivery systems" also include transdermal patches containing the ingredient to be administered. Delivery through the skin can further be achieved by iontophoresis or electro transport, if desired.

Formulations for topical administration to the skin include, for example, ointments, creams, gels and pastes comprising the fungal iron acquisition inhibitor in a pharmaceutical acceptable carrier. The formulation of fungal iron acquisition inhibitors for topical use includes the preparation of oleaginous or water-soluble ointment bases, as is well known to those in the art. For example, these formulations may include vegetable oils, animal fats, and, for example, semisolid hydrocarbons obtained from petroleum. Particular components used may include white ointment, yellow ointment, cetyl esters wax, oleic acid, olive oil, paraffin, petrolatum, white petrolatum, spermaceti, starch glycerite, white wax, yellow wax, lanolin, anhydrous lanolin and glyceryl monostearate. Various water-soluble ointment bases may also be used, including glycol ethers and derivatives, polyethylene glycols, polyoxyl 40 stearate and polysorbates.

Subjects affected with corneal fungal infection (or at risk of corneal fungal infection), which are not readily accessible or suitable for ophthalmic (e.g. eye-drops) and/or topical administration, can be treated by a systemic approach, such as intravenous infusion. For example, the fungal iron acquisition inhibitor can be administered at a low dosage by continuous intravenous infusion. In another example, in which a patient requires longer-term care, the fungal iron acquisition inhibitor can be administered intermittently (e.g., every 6-24 hours). In a variation of this approach, the initial or loading dose can be followed by maintenance doses that are less than, (e.g., half) the loading dose or by continuous infusion. The duration of such treatment can be determined by those having skill in the art, based on factors, for example, the severity of the condition and the observation of improvements.

When administering the fungal iron acquisition inhibitor to the subject by intravenous infusion, devices and equipment (e.g., catheters, such as central or peripheral venous catheters, tubing, drip chambers, flashback bulbs, injection Y sites, stopcocks, and infusion bags) can be used that are compatible with the fungal iron acquisition inhibitor.

Embodiments described herein also relate to a coating for a medical device. Coatings including fungal iron acquisition inhibitors can be applied to a number of medical device materials known in the art in order to coat medical/surgical devices and permanent medical/surgical implants. A coating including a fungal iron acquisition inhibitor described herein can be provided on at least a portion of the medical device.

Percutaneous devices (such as catheters) and implanted medical devices (including, but not limited to, pacemakers, vascular grafts, stents, and heart valves) commonly serve as foci for bacterial infection. The tendency of some microorganisms (e.g., *Candida*) to adhere to and colonize the surface of the device, promotes such infections, which increase the morbidity and mortality associated with use of the devices. Therefore, in some embodiments, a fungal iron acquisition inhibitor or pharmaceutical compositions thereof can be used to treat or prevent fungal infection on a medical device by contacting the device with a fungal iron acquisition inhibitor or pharmaceutical composition thereof in an amount effective to treat fungal infection or inhibit fungal growth when implanted in a subject. For example, in certain embodiments of the present invention, the coating can include an amount of one or more fungal iron acquisition inhibitors effective to treat fungal infection or inhibit fungal growth related to *Candida* when implanted in a subject.

A medical device as described herein can include any instrument, implement, machine, contrivance, implant, or other similar or related article, including a component or part, or accessory which is: recognized in the official U.S. National Formulary the U.S. Pharmacopoeia, or any supplement thereof; intended for use in the diagnosis of disease or other conditions, or in the cure, mitigation, treatment, or prevention of disease, in humans or in other animals; or, intended to affect the structure or any function of the body of humans or other animals, and which does not achieve any of its primary intended purposes through chemical action within or on the body of human or other animal, and which is not dependent upon being metabolized for the achievement of any of its primary intended purposes.

A medical device can include, for example, endovascular medical devices, such as intracoronary medical devices. Examples of intracoronary medical devices can include stents, drug delivery catheters, grafts, and drug delivery balloons utilized in the vasculature of a subject. Where the medical device comprises a stent, the stent may include peripheral stents, peripheral coronary stents, degradable coronary stents, non-degradable coronary stents, self-expanding stents, balloon-expanded stents, and esophageal stents. The medical device may also include arterio-venous grafts, by-pass grafts, penile implants, vascular implants and grafts, intravenous catheters, small diameter grafts, surgical mesh, artificial lung catheters, electrophysiology catheters, bone pins, suture anchors, blood pressure and stent graft catheters, breast implants, benign prostatic hyperplasia and prostate cancer implants, bone repair/augmentation devices, breast implants, orthopedic joint implants, dental implants, implanted drug infusion tubes, oncological implants, pain management implants, neurological catheters, central venous access catheters, catheter cuff, vascular access catheters, urological catheters/implants, atherectomy catheters, clot extraction catheters, PTA catheters, PTCA catheters, stylets (vascular and non-vascular), drug infusion catheters, angiographic catheters, hemodialysis catheters, neurovascular balloon catheters, thoracic cavity suction drainage catheters, electrophysiology catheters, stroke therapy catheters, abscess drainage catheters, biliary drainage products, dialysis catheters, central venous access catheters, and parental feeding catheters.

The medical device may additionally include either arterial or venous pacemakers, vascular grafts, sphincter devices, urethral devices, bladder devices, renal devices, gastroenteral and anastomotic devices, vertebral disks, hemostatic barriers, clamps, surgical staples/sutures/screws/plates/wires/clips, glucose sensors, blood oxygenator tubing, blood oxygenator membranes, blood bags, birth control/IUDs and associated pregnancy control devices, cartilage repair devices, orthopedic fracture repairs, tissue scaffolds, CSF shunts, dental fracture repair devices, intravitreal drug delivery devices, nerve regeneration conduits, electrostimulation leads, spinal/orthopedic repair devices, wound dressings, embolic protection filters, abdominal aortic aneurysm grafts and devices, neuroaneurysm treatment coils, hemodialysis devices, uterine bleeding patches, anastomotic closures, aneurysm exclusion devices, neuropatches, vena cava filters, urinary dilators, endoscopic surgical and wound drainings, bandages, surgical tissue extractors, transition sheaths and dialators, coronary and peripheral guidewires, circulatory support systems, tympanostomy vent tubes, cerebro-spinal fluid shunts, defibrillator leads, percutaneous closure devices, drainage tubes, bronchial tubes, vascular coils, vascular protection devices, vascular intervention devices including vascular filters and distal support devices and emboli filter/entrapment aids, AV access grafts, surgical tampons, and cardiac valves.

The medical device can include any material known in the art including, for example, biocompatible polymers, such as PTFE, ePTFE, poly(ethylene co-vinyl alcohol) (pEVOH) and silicone, metals and metal alloys, such as gold, NITINOL, NiTi and titanium, and glass. Other examples of suitable biocompatible polymers can include polyalkylene oxides, polymethacrylates, polyurethanes, cellulosics, polyhydroxyalkyl acrylates, polyesters, and polymers comprised of at least one polyethylene monomer, such as polyethylene glycol (PEG) or polyethylene oxide, polymers comprised of polyamine monomers, such as polyethyleneimine (PEI), and poly(L-lactide) (PLLA), poly-p-dioxanone (PDO), polycaprolactone (PCL), polyvinyl alcohol (PVA), and poly(lactide-co-glycolide) (PLG).

Still other embodiments relate to a contact lens for treating corneal fungal infection in a subject. The contact lens includes a contact lens substrate and a coating provided on at least a portion of the substrate. The coating can include an amount of fungal iron acquisition inhibitor effective to treat a fungal infection and related inflammation in a subject upon administration of the contact lens to the subject.

Coatings including fungal acquisition inhibitors described herein or combinations thereof can be applied to a number of contact lens substrate materials known in the art. Virtually any substrate known in the art that can be fashioned into a contact lens can be used in the present invention provided it is optically transparent.

In some embodiments, the substrate can include optically transparent materials that allow oxygen to reach the cornea in an amount, which is sufficient for long-term corneal health. Examples of substrates include polymers made from hydrophobic materials, such as silicone copolymers, interpolymers, oligomers, and macromers. Illustrative polysilicones are polydimethyl siloxane, polydimethyl-co-vinylmethylsiloxane. Other silicones include silicone rubbers described in U.S. Pat. No. 3,228,741 to Becker; blends such as those described in U.S. Pat. No. 3,341,490 to Burdick et al., and silicone compositions such as described in U.S. Pat. No. 3,518,324 to Polmanteer. Substrates described in U.S. Pat. Nos. 4,136,250; 5,387,623; 5,760,100; 5,789,461; 5,776,999; 5,849,811; 5,314,960 and 5,244,981 can also be used in the invention. Cross-linked polymers of propoxylate of methyl glucose and propylene oxide and HEMA-based hydrogels can also be used as substrates of the contact lens.

Silicone compositions that can be used in forming the contact lens of this invention are the cross-linked polysiloxanes obtained by cross-linking siloxane prepolymers by means of hydrosilylation, co-condensation and by free radical mechanisms such those described by Chen in U.S. Pat. No. 4,143,949, which is incorporated herein by reference. Additional silicone-based substrates are cross-linked polymers of α,ω-bisamionpropyl polydimethylsiloxane, and gylycidyl methacrylate, cross-linked polymers. Silicone compositions also contemplated by the present invention are made from combining a methacrylate with one or more silicone monomers in the presence of a group transfer polymerization (GTP) catalyst to form a macromer that is subsequently polymerized with other monomers to give the final substrate. Initiators, reaction conditions, monomers, and catalysts that can be used to make group transfer (GTP) polymers are described in "Group Transfer Polymerization" by O. W. Webster, in Encyclopedia of Polymer Science and Engineering Ed. (John Wiley & Sons) p. 580, 1987. Substrates described in U.S. Pat. No. 6,951,894 are also suitable for use in the present invention.

The coating can be prepared and applied as an aqueous solution, suspension, or colloid and then applied to the contact lens substrate according to any process that can provide the coating in contact with the substrate. For example, processes for applying the coating to the substrate include immersion, spraying, brushing, and spin coating. Once the lens substrate is coated it may be subjected to any number of additional steps that are conducted in the manufacture of contact lenses. These can include, for example, swelling and washing steps, the addition of additives such as surfactants, extraction steps and the like.

The coating including the fungal iron acquisition inhibitor can adhere to the contact lens by, for example, chemical bonding, such as covalent or ionic bonding, or physical bonding. In some aspects, the coating can remain affixed to the lens substrate throughout its useful life (e.g., storage time plus the time in which it will be in contact with a user's eye).

The contact lens can also include more than one layer of coating. This can be desirable where the coating layer will provide the requisite surface properties (e.g. treatment of corneal fungal infection) but is not particularly compatible with the lens substrate itself. For example, a tie-layer or coupling agent can be used to adhere the coating to the substrate. Selections of compatible lens substrate, thioredoxin protein inhibitor coating, and tie-layer (if necessary) materials is well within the knowledge of one skilled in the art.

In some embodiments, the contact lens is non-toxic to the subject's cornea and other tissue while providing for the treatment of corneal fungal infection in the subject.

Other embodiments relate to an ophthalmic solution for treating corneal fungal infection in a subject. The solution can be aqueous and include a fungal iron acquisition inhibitor as described above. Examples of solutions useful that can be used in the treatment of corneal fungal infection and related inflammation include solutions that are contacted with eye lids and/or eyes, such as multipurpose lens solutions, ophthalmalic rinse solutions, surgical scrubs for eye use, eye drops, eye wash solutions, contact lens solutions, topical over the counter ocular and periocular solutions (i.e. artificial tears), ocular and periocular cleaning solutions, eye irrigating solutions, and/or antibacterial solutions for surgical scrubs or topical application.

In some aspects, a fungal iron acquisition inhibitor may be added to a commercially available contact lens solution or a multipurpose lens solution to treat corneal fungal infection and related inflammation. In other aspects, a fungal iron acquisition inhibitor may be added to an aqueous solution prepared for use as a contact lens or multipurpose lens solution that is not commercially available to treat corneal fungal infection.

In some aspects where the ophthalmic solution includes a cleaning solution, the cleaning solution can include cleaning agents to effectively clean a lens of film deposits and surface debris. Examples of cleaning agents that can be used include, poloxamers and tetronic surfactants comprising poly(oxythylene) hydrophilic units. In all embodiments, the cleaning agents are nontoxic, and do not distort the vision of the subject being treated for corneal fungal infection.

In other aspects, fungal iron acquisition inhibitor may be added to tonicity agents and buffers that are found in conventional ophthalmic solutions. Examples of tonicifiers include dextrose, potassium chloride and/or sodium chloride. Examples of buffers include boric acid, sodium borate, sodium or potassium citrate, sodium bicarbonate, sodium phosphate, and potassium phosphate.

Additionally, antibacterial agents found in conventional ophthalmic solutions, such as multipurpose lens solutions, may be added. Antibacterial agents for use in the solution include, for example, polyaminopropyl biguanide, alexidine hydrochloride, polyquaternium-1, polyquaternium 42, myristamidopropyl dimethylamine, or other agents known to those skilled in the art.

In some aspects, the solution may further include a comfort or moisturizing agent to provide hydration and lubrication of a subject's contact lens. Such agents include, for example, polyquaternium 10, poloxamer, propylene glycol, hydroxypropylmethylcellulose (HPMC), or other agents known to those skilled in the art.

Since, in some aspects, the solution is intended to be administered topically to the eyelids and/or eye, it is contemplated that the solution be free of pathogenic organisms and/or sterile. A benefit of a sterile solution is that it reduces the possibility of introducing contaminants into a subject's eyelids and/or eye. Sterility or adequate antimicrobial preservation may be provided as part of the present solutions of the present invention. In some aspects, the solutions are produced under sterile conditions.

In addition to or in place of sterilization, aqueous solutions of the fungal iron acquisition inhibitor may contain a physiologically acceptable preservative to minimize the possibility of microbial contamination. A physiologically acceptable preservative may be used in the solutions of the present invention to increase the stability of the solutions. Preservatives include, for example, polyaminopropyl biguanide, polyhexamethylene biguanide (PHMB), polyquaternium-1, myristamidopropyl, and sorbic acid.

In yet another aspect, the fungal iron acquisition inhibitors and methods of their use described herein can be administered to a subject or applied to a device as part of a combinatorial therapy with additional therapeutic agents. The phrase "combinatorial therapy" or "combination therapy" embraces the administration of a fungal iron acquisition inhibitor, and one or more therapeutic agents as part of a specific treatment regimen intended to provide beneficial effect from the co-action of these therapeutic agents. In certain aspects, the phrase "combinatorial therapy" or "combination therapy" embraces the administration of a first fungal iron acquisition inhibitor and a second fungal iron acquisition inhibitor described herein.

Administration of these therapeutic agents in combination typically is carried out over a defined period (usually minutes, hours, days or weeks depending upon the combination selected). "Combinatorial therapy" or "combination therapy" is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example by administering to the subject an individual dose having a fixed ratio of each therapeutic agent or in multiple, individual doses for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissue. The therapeutic agents can be administered by the same route or by different routes. The sequence in which the therapeutic agents are administered is not narrowly critical.

For example, in certain aspects, a combination therapy can include the administration of both an iron chelator and a siderophore biosynthesis inhibitor of the invention. In an exemplary embodiment, an ophthalmic preparation topically administered to a subject 0 and 6 h post infection for the treatment of a corneal fungal infection includes a first fungal iron acquisition inhibitor, the iron chelator deferiprone (11.1 μg in 80 of commercially available eye drop formulation, Alcon Laboratories) and a second fungal iron acquisition inhibitor, the statin drug simivastatin (13.4 μg in 8 μl of commercially available eye drop formulation, Alcon Laboratories).

In other embodiments, the fungal iron acquisition inhibitor (e.g., iron chelator and/or asiderophore biosynthesis inhibitor) can be administered in combination with a thioredoxin protein inhibitor to treat a fungal infection of a subject. The thioredoxin protein inhibitor can include any agent that when administered to a subject having a fungal infection is capable of binding to the active site of thioredoxin protein in a fungal cell and inhibits the protein's ability to partake in redox reactions and quench cytoplasmic ROS and thus inhibit the fungal cell's ability to minimize cellular damage from both exogenous and endogenous ROS sources.

In some embodiments, a thioredoxin protein inhibitor is effective in the treatment of fungal infection by enhancing fungal cell susceptibility to killing by endogenous neutrophils of the subject. In other embodiments, a thioredoxin protein inhibitor is effective in killing fungal cells in a subject in the absence of neutrophils.

In some embodiments, the thioredoxin protein inhibitor is a disulfide that has a molecular weight of less than about 350 g/mole. In other embodiments, the thioredoxin protein inhibitor is a disulfide that has a molecular weight of less than about 300 g/mole, less than about 250 g/mole, or less than about 200 g/mole. Examples of disulfides In one embodiment, the thioredoxin protein inhibitor can include a asymmetrical or symmetrical disulfide having a molecular weight of less than about 350 g/mole and the formula R$_1$—S—S—R$_2$ wherein R$_1$ and R$_2$ may be the same and independently represent an alkyl, an arylalkyl, an imidazole thiadiazole, thiazole, benzimidazole, purine, phenyl, benzyl, phenylethyl, pyridine, pyrimidine, benzoxazole, benzthiazole, cycloalkyl, hydroxylalkyl, carboxyalkyl, haloalkyl, catopril, or cycloalkanone.

In another embodiment, the thioredoxin protein inhibitor can include a asymmetrical or symmetrical disulfide having a molecular weight of less than about 350 g/mole and the formula R$_1$—S—S—Y—S—S—R$_2$, wherein R$_1$ and R$_2$ and Y may be the same and are independently selected from the group described above with Y being selected from the group consisting of alkyl, hydroxyalkyl, arylalkyl, and thiadiazoles.

Examples of thioredoxin protein inhibitors that include an asymmetrical or a symmetrical disulfide having a molecular weight of less than about 350 g/mole and the formula R$_1$—S—S—R$_2$ or R$_1$—S—S—Y—S—S—R$_2$ are described in U.S. Pat. No. 6,552,060, which is herein incorporated by reference in its entirety.

In another embodiment of the present invention, a thioredoxin protein inhibitor used to treat fungal infection in the subject can include an imidazole disulfide compound having the general formula (I):

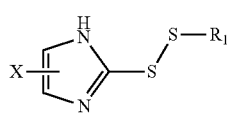

(I)

and pharmaceutically acceptable salts thereof.

In certain embodiments, R$_1$ may be independently selected from alkyl, arylalkyl, an imidazole thiadiazole, thiazole, benzimidazole, purine, phenyl, benzyl, phenylethyl, pyridine, pyrimidine, benzoxazole, benzthiazole, cycloalkyl, hydroxylalkyl, carboxyalkyl, haloalkyl, catopril, and cycloalkanone. In an exemplary embodiment, R$_1$ is a branched alkyl group.

Generally, the X group is optional and when present may be any common functional group described herein including, but not limited to, alkyl, alkoxy, hydroxyl, carboxy, carbaldehyde, amino, halo, keto, nitro and combinations thereof.

In an exemplary embodiment, the thioredoxin protein inhibitor is the small molecule PX-12 (1-methylpropyl 2-imidazolyl disulfide), having the structure:

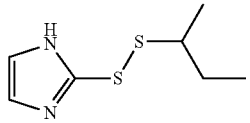

PX-12 or a pharmaceutically acceptable salt thereof.

A thioredoxin protein inhibitor used in methods described herein can also include a PX-12 analog and/or derivative thereof. Regardless of the thioredoxin protein inhibitor employed, the thioredoxin protein inhibitors can be administered to achieve at least transient blockade of thioredoxin protein function, thereby at least partially neutralizing or inhibiting the antioxidant effect of thioredoxin protein in fungal cells.

In other embodiments, the fungal iron acquisition inhibitor (e.g., iron chelator and/or asiderophore biosynthesis inhibitor) can be administered in combination with a zinc transport inhibitor to treat a fungal infection of a subject. Zinc is required for function of a number of enzymes, including zinc superoxide dismutase, which is important in the fungal antioxidant response and is essential for fungal growth and survival.

In some embodiments the zinc transport inhibitor can include a zinc chelator that is capable of inhibiting fungal survival in the presence of neutrophils. For example, the zinc chelator may selected from the group consisting of ethylenediaminetetra-acetic acid (EDTA), 1,3-diaminopropane-N,N,N',N'-tetraacetic acid (DTPA), N,N,N',N'-tetrakis (2-pyrdiylmethyl)ethylenediamine (TPEN), 1,10-phenanthroline, clioquinol, diethyldithiocarbamate (DEDTC), 2,3-dimercapto-1-propanesulfonic acid (DMPS), ethylenediamine-N,N'-diacetic-N,N'-di-B-propionic acid (EDPA), 1,2-dimethyl-3-hydroxy-4-pyridinone (DMHP), 1,2-diethyl-3-hydroxy-4-pyridinone (DEHP), ethylmaltol (EM), 4-(6-Methoxy-8-quinaldinyl-aminosulfonyl)benzoic acid potassium salt (TFLZn), dithiozone, N-(6-methoxy-8-quinolyl)-para-toluenesulfonamide (TSQ), carnosine, deferasirox, trans-1,2-cyclohexane-diamine-N,N,N',N'-tetraacetic acid (CyDTA), dihydroxyethylglycine (DHEG), 1,3-diamino-2-hydroxypropane-N,N,N',N'-tetraacetic (DTPA-OH), ethylenediamine-N,N'-diacetic acid (EDDA), ethylenediamine-N,N'-dipropionic acid (EDDP), ethylenediamine-N,N'-bis(methylphosphonic) acid (EDDPO), N-hydroxy-ethylenediamine-N,N',N'-triacetic acid (EDTA-OH), ethylenediaminetetra(methylenephosphonic) acid (EDTPO), N,N'-bis(2-hydroxybenzyl)ethylenediamine-N, N'-diacetic acid (HBED), hexamethylene-1,6-diaminetetraacetic acid (HDTA), hydroxyethyliminodiacetic acid (HIDA), iminodiacetic acid (IDA), Methyl-EDTA, nitrilotriacetic acid (NTA), nitrilotripropionic acid (NTP), Nitrilotrimethylenphosphonic acid (NTPO), 7,19,30-trioxa-1,4,10, 13,16,22,27,33-octaazabicyclo[11,11,11]pentatriacon-tane (O-Bistren), triethylenetetraaminehexaacetic acid (TTHA), ethyleneglycol bis(2-Aminoethyl ether)-N,N,N',N'-tetraacetic acid (EGTA), dimercaptosuccinic acid (DMSA), deferoxamine, dimercaprol, zinc citrate, combination of bismuth and citrate, penicilamine, succimer, Etidronate, ethylenediamine-di(O-hydroxyphenylacetic acid) (ED-DHA), trans-1,2-cyclohexanediaminetetraacetic acid (CDTA), N-(2-hydroxyethyl)ethylenedinitrilotriacetic acid (HEDTA), N-(2-hydroxyethyl)iminodiacetic acid (HEIDA), calprotectin, zinc fingers, lactoferrin, ovotransferrin, conalbumin, and combinations thereof. In other embodiments, the zinc transport inhibitor can include an antimalarial agent, such as atovaquone and/or halofantrine, which were found to block zinc homeostasis in yeast.

In still other embodiments, the fungal iron acquisition inhibitor (e.g., iron chelator and/or asiderophore biosynthesis inhibitor) can be administered in combination with a spleen tyrosine kinase inhibitor (syk) to treat a fungal infection of a subject. The earliest responses to fungal infection in a subject include elevated expression of pathogen recognition molecules, including c-type lectins, Dectin-1 and Dectin-2, which respond to cell wall β-glucan and α-mannan residues. Both regulators activate NFκB through syk phosphorylation. It was found that blocking syk phosphorylation with a syk inhibitor can inhibit fungal infection and subject mediated inflammation in a subject with a fungal infection.

In some embodiments, the syk inhibitors include, but are not limited to the following compounds: 2-[7-(3,4-dimethoxyphenyl)-imidazo[1,2-c]pyrimidin-5-ylamino]-nicotinamid-e dihydrochloride, 2-(2-aminoethylamino)-4-(3-methylanilino) pyrimidine-5-carboxamide, 2-(2-aminoethylamino)-4-(3-trifluoromethylanilino)pyrimidine-5-carboxamid-e, 2-(4-aminobutylamino)-4-(3-trifluoromethylanilino)pyrimidine-5-carboxam-ide, 2-(2-aminoethylamino)-4-(3-bromoanilino)pyrimidine-5-carboxamide, 2-(2-aminoethylamino)-4-(3-nitroanilino) pyrimidine-5-carboxamide, 2-(2-aminoethylamino)-4-(3,5-dimethylanilino)pyrimidine-5-carboxamide, 2-(2-aminoethylamino)-4-(2-naphthylamino)pyrimidine-5-carboxamide, 2-(cis-2-aminocyclohexylamino)-4-(3-methylanilino)pyrimidine-5-carboxamid-e, 2-(cis-2-aminocyclohexylamino)-4-(3-bromoanilino)pyrimidine-5-carboxami-de, 2-(cis-2-aminocyclohexylamino)-4-(3,5-dichloroanilino)pyrimidine-5-car-boxamide and 2-(cis-2-aminocyclohexylamino)-4-(3,4,5-trimethoxyanilino) pyrimidine-5-ca-rboxamide, NVP-QAB205, piceatannol, 4-(3-(2H-1,2,3-triazol-2-yl)phenylamino)-2-((1R,2S)-2-aminocyclohexylamin-o)pyrimidine-5-carboxamide acetate (P505-15), and 3,4-dimethyl-10-(3-aminopropyl)-9-acridone oxalate.

Additional examples of syk inhibitors are found in the following publications, all of which are herein incorporated by reference in their entirety: U.S. Patent Publication No. 2013/0274216 entitled, "Treatment for Microbe-Induced Inflammatory responses in the eye"; U.S. Patent Publication No. 2012/0329780 entitled "Novel kinase Inhibitors"; U.S. Pat. No. 7,671,063 entitled "2,4 Di (hetero)-arylaminopyrimidine derivatives as ZAP-70 and/or syk inhibitors"; U.S. Patent Publication No. 2008/0139531 entitled "Use of connective tissue mast cell stabilizers to facilitate ocular surface re-epithelization and wound repair"; U.S. Pat. No. 8,063,058 entitled "Inhibitors of syk and JAK protein kinases"; U.S. Pat. No. 8,138,339 entitled "Inhibitors of protein kinases"; U.S. Patent Publication No. 2011/0053897 entitled "Compounds and compositions as syk kinase inhibitors"; WO2011/014795 entitled "Compounds and compositions as syk kinase inhibitors"; WO2010/146133 entitled "Heterocyclylaminopyrimidines as kinase inhibitors"; WO2010/097248 entitled "Pyrimidinecarboxamide derivatives as inhibitors of syk kinase"; U.S. Patent Publication No. 2010/0222323 entitled "Imidazopyrazine syk inhibitors"; U.S. Patent Publication No. 2010/0093698 entitled "Aminotriazolopyridines, compositions thereof, and methods of treatment therewith"; U.S. Patent Publication No. 2011/0201608 entitled "Substituted naphthyridines and use thereof as medicines"; U.S. Patent Publication No. 2011/0112098 entitled "Molecules inhibiting a metabolic pathway involving the syk protein tyrosine kinase and method for identifying said molecules"; and U.S. Patent Publication No. 2012/0329780 entitled "Novel kinase inhibitors".

In still other embodiments, the combinational therapy can include the administration of a fungal iron acquisition inhibitor with at least one antibacterial, antiviral or antifungal agent to treat a microbial infection and related inflammation (e.g., corneal inflammation) in a subject. Antibiotic agents administered in conjunction with a thioredoxin protein inhibitor or pharmaceutical composition can include, but are not limited to aminosalicylic acid, nalidixic acid, amoxicillin, amoxicillin and potassium clavulanate, ampicillin, ampicillin and sulbactam, azithromycin, bacampicillin, carbenicillin indanyl sodium (and other carbenicillin salts), capreomycin, cefadroxil, cefazolin, cephalexin, cephalothin, cephapirin, cephaclor, cefprozil, cephadrine, cefamandole, cefonicid, ceforanide, cefuroxime, cefixime, cefoperazone, cefotaxime, cefpodoxime, ceftazidime, ceftibuten, ceftizoxime, ceftriaxone, cefepime, cefmetazole, cefotetan, cefoxitin, ciprofloxacin, clarithromycin, clindamycin, clofazimine, cloxacillin, co-trimoxazole, cycloserine, dicloxacillin, dirithromycin, erythromycin (and erythromycin salts such as estolate, ethylsuccinate, gluceptate, lactobionate, stearate), ethambutol-HCl and other salts, ethionamide, fosfomycin, gentamycin (fortified with vancomycin for methicillin-resistant *Staphylococcus aureus* (MRSA) infections) imipenem, isoniazid, levofloxacin, lomefloxacin, loracarbef, methicillin, methenamine, metronidazole, mezlocillin, nafcillin, nitrofurantoin, norfloxacin, novobiocin, ofloxacin, oxacillin, penicillin V, penicillin salts, penicillin complexes, pentamidine, piperacillin, piperacillin and tazobactam, sparfloxacin, sulfacytine, sulfamerazine, sulfamethazine, sulfamethizole, sulfasalazine, sulfisoxazole, sulfapyrazine, sulfadiazine, sulfinethoxazole, sulfapyridine, ticarcillin, ticarcillin and potassium clavulanate, trimethoprim, trimetrexate, troleandomycin, $4^{th}$ generation fluroquinoline like moxifloxacin or gatifloxacin, cefazolin or vancomycin and fluoroquinolone vancomycin and mixtures thereof.

In one specific example, the combinational therapy includes a fungal iron acquisition inhibitor and at least one ophthalmic antibiotic or ophthalmic antiviral. Ophthalmic antibiotics include, for example, chloramphenicol sodium succinate ophthalmic (chloramphenical); CORTISPORIN (neomycin and polymyxin β sulfates and hydrocortisone acetate cream); ILOTYCIN (erythromycin ophthalmic ointment); NEODECADRON (neomycin sulfate-dexamethasone sodium phosphate); POLYTRIM (trimethoprim and polythyxin β sulfate opthalmic solution); TERRA-CORTRIL (oxytetracycline HCL and hydrocortisone acetate); TERRAMYCIN (oxytetratcycline); and TOBRADEX (tobramycin and dexamethosone ophthalmic suspension and ointment).

Ophthalmic antivirals include, for example, VIRA-A ophthalmic ointment, (vidarabine). Opthalmic quinalones include, for example, CHIBROXIN (norfloxacin ophthalmic solution); CILOXAN ophthalmic solution, (Ciprofloxacin HCL); and Ocuflox ophthalmic solution (ofloxacin). Opthalmic sulfonamides include, for example, BLEPHAMIDE ophthalmic ointment (sulfacetamide sodium and prednisolone acetate); and BLEPHAMIDE ophthalmic suspension (sulfacetamide sodium and prednisolone acetate).

Additionally, a fungal iron acquisition inhibitor may be administered to a subject for the treatment of a fungal infection in combination with one or more other antifungal agents, such as a polyenic derivative (e.g. Amphotericin B, Nystatin, a lipid formulation of Amphotericin B, filipin and/or pimaricin (Natamycin)), 5-fluctyosine, an azole derivative (e.g., Voriconazole Fluconazole, Intraconazole, Ketoconazole, Miconazole, Clotrimazole, ZD-08070, UK-109496, SCH 56592), 5 Fluorocytosine, a Pneumocandin or Echinocandin derivative such as Cilofungin, LY-303366, L 733560, or L-743872.

The invention is further illustrated by the following example, which is not intended to limit the scope of the claims.

Example

We examined the role of host iron sequestration and fungal iron acquisition in a murine model of *Aspergillus* and

*Fusarium* corneal infection. We show that Dectin-1 and IL-6 regulate expression of genes involved in iron sequestration and that fungal growth positively correlates with serum iron levels. Using mutant *A. fumigatus* and *F. oxysporum* strains, we also demonstrate that fungal transcriptional responses to low iron levels and mevalonic acid-dependent extracellular siderophore biosynthesis but not intracellular siderophores or reductive iron assimilation are essential for fungal growth. Lastly, using iron chelators, siderophore binding proteins, and siderophore biosynthesis inhibitors we demonstrate that targeting fungal iron acquisition enhances fungal clearance from infected tissues.

Materials and Methods

Use and Source of Animals

All animals were treated in accordance with the guidelines provided in the Association for Research in Vision and Ophthalmology ARVO statement for the Use of Animals in Ophthalmic and Vision Research, and were approved by Case Western Reserve University IACUC.

Fungal Strains and Growth Conditions

Table 1 lists the genotype and phenotype of all strains utilized in this study. *Aspergillus fumigatus* was cultured on Vogel's minimal media (VMM)+2% agar and *Fusarium oxysporum lycopersici* was cultured on potato dextrose agar (PDA). *Alternaria brassicicola* was cultured in complete media as described previously. All solid media used in this study were supplemented with 10 mM FeSO4 to enhance conidia production by siderophore mutants. For neutrophil-fungus incubation assays, all fungi were grown in RPMI media w/o FeSO4 supplementation.

TABLE 1

Fungal strains utilized in this study

| Strain | Genotype | Phenotype |
|---|---|---|
| *A.fumigatus* | | |
| Af-dsRed | Af293.1 - ΔpyrG1::gdpA::dsRed::pyrG | dsRed Fluorescence |
| ATCC 46645 | | WT |
| ΔsidA | ATCC 46645- ΔsidA::hph | No intra or extracellular siderophores |
| ΔsidC | ATCC 46645- ΔsidC:: hph | No intracellular siderophores |
| ΔsidD | ATCC 46645- ΔsidD:: hph | No fusarinine C or TAFC |
| ΔsidF | ATCC 46645-ΔsidF:: hph | No extracellular siderophores |
| ΔsidG | ATCC 46645- ΔsidG:: hph | No TAFC |
| ΔsidH | ATCC 46645- ΔsidH:: hph | No extracellular siderophores |
| ΔsidI | ATCC 46645- ΔsidI:: hph | No extracellular siderophores |
| ΔhapX | ATCC 46645- ΔhapX:: hph | No hapX |
| *F.oxysporum* | | |
| FoxL--4287 | | WT |
| ΔhapX | 4287- ΔhapX::hph | No hapX |
| *A. brassicicola* | | |
| WT-Tf383 | | WT |
| Δnps2 | Tf383- nps2; hph | No intracellular siderophores |
| Δnps6 | Tf383- nps6; hph | No extracellular siderophores |
| Δnps2/6 | Tf383- nps2; hph | No intra or extracellular siderophores |

Mouse Model of *Aspergillus* and *Fusarium* Keratitis and Drug Treatments

*Aspergillus* and *Fusarium* strains were cultured as described above for 2-3 days, and fresh conidia were disrupted with a bacterial L-loop, harvested in 5 ml PBS, and filtered through sterile PBS soaked cotton gauze in a 10 ml syringe to obtain pure conidial suspensions. Conidia were quantified using a hemocytometer and adjusted in PBS to a final stock solution of 15-20,000 conidia/μl. Mice were anaesthetized with 1.25% 2, 2, 2-tri-bromoethanol in PBS. The corneal epithelium was abraded using a 30-gauge needle, through which a 2 μl injection containing conidia was released into the corneal stroma using a 33-gauge Hamilton syringe. Mice were examined daily under a stereomicroscope for corneal opacification, and quantified by image analysis using Metamorph software as described. At each time point, animals were euthanized by $CO_2$ asphyxiation, and eyes were either placed in 10% formalin and embedded in paraffin, sectioned at 5 μm intervals and stained with periodic acid schiff and hematoxylin (PASH), or were placed in 1 ml of sterile PBS, homogenized and colony forming units (CFU) were quantified by manual count.

For topical drug delivery, compounds were suspended in a commercial eye drop formulation (Alcon laboratories) or in PBS and 8 μl applied topically at 0 h and 6 h post-infection. Lactoferrin (1.25 mg/ml), deferiprone (10 mM), deferroxamine (10 mM), and simvastatin (4 mM) were purchased from Sigma Aldrich (St. Louis, Mo.). BEC (28 mM) was obtained from Cayman chemicals (Ann Arbor, Mich.). *E. coli*-expressed recombinant human lipocalin-1 was purified as described previously and applied topically at 2 mg/ml. Iron-dextran and deferroxamine were both purchased from Sigma and administered systemically to mice via daily I.P. injections of 5 mg starting at day-2 until mice were euthanized. All animals were bred under specific pathogen-free conditions and maintained according to institutional guidelines.

Quantification of *Aspergillus* Fungal Mass and Colony Forming Units (CFUs)

Growth of the RFP expressing *A. fumigatus* strain in the cornea was detected using fluorescent microscopy and quantified by Metamorph image analysis. For assessment of fungal viability, whole eyes were homogenized under sterile conditions in 1 ml PBS, using the Mixer Mill MM300 (Retsch) at 33 Hz for 4 min. Subsequently, 100 μl aliquots were plated onto bacteriologic-grade sabouraud dextrose agar plates, incubated for 24 h at 37° C. (*Aspergillus*) or at 30° C. (*Fusarium* and *Alternaria*), and the number of CFUs was determined by direct counting.

Quantification of IL-6 Protein in Mouse Corneas and Serum

Corneas were homogenized in 150 μl reagent diluent (R & D Systems, Minneapolis, Minn.) using the Retsch MM 300 ball miller at 33 Hz for 4 min (Qiagen). Mouse serum was obtained as described below and assayed directly. IL-6 protein was quantified using a mouse IL-6 ELISA kit as per manufacturer's instructions (R & D Systems, Minneapolis, Minn.).

Quantification of Neutrophils in Mouse Corneas

Corneas were dissected, cut into 8 small fragments, and incubated in 80 units of collaganese (Sigma-Aldrich) for 1-2 h. The cell suspensions were filtered, centrifuged at 300*g for 5 min at 4° C. and washed in FACS buffer (PBS+1% FBS+0.5% Na azide). Cells were then incubated with anti-mouse CD16/32 antibody (Fc block, clone 93, eBioscience) for 10 min followed immediately by incubation with biotinylated rat anti-mouse NIMP-R14 or isotype control for 45 min. Cells were washed and incubated with streptavidin-PE-Cy7 for 30 min in the dark. Cell suspensions were then analyzed utilizing a C6 Accuri flow cytometer with gates set based on isotype controls.

Quantitative PCR of Infected Corneas

C57BL/6 mice or IL-6–/– mice were infected with *A. fumigatus* strain Af-dsRed as described above. At 24 h mice were sacrificed, corneas were excised, suspended in tissue lysis buffer (Qiagen, Valencia, Calif.) and homogenized using the Mixer Mill MM300 (Retsch) at 33 Hz for 2 min. Subsequently, RNA was extracted from samples using RNeasy mini kit according to the manufacturer's directions (Qiagen, Valencia, Calif.). Samples with a 260/280 (RNA: protein) ratio of 2.0 were used to generate cDNA using the superscript first strand synthesis system (Life technologies, Grand Island, N.Y.) using standard methods. Real Time PCR was performed on the cDNA samples using the SYBR green system (Applied Biosystems, Carlsbad, Calif.). All primers used in this study are listed in Table 2 and were synthesized by Integrated DNA technologies (San Diego, Calif.). Fold change with respect to naïve uninfected corneas was calculated using the $2^{-\Delta\Delta ct}$ method. Data are therefore presented as fold increases of relative gene expression (log (RQ)). RT-PCR samples were also analyzed by 2% agarose gel electrophoresis.

TABLE 2

Primers sequence and protein function

| Primer | Source (PB ID) | Sequence | Protein Function |
|---|---|---|---|
| Iron Chelation | | | |
| Lactoferrin | 141803548b2 | CCGCTCAGTTGTG TCAAGAAA (SEQ ID NO: 1) CATGGCATCAGCTCTGTTTGT (SEQ ID NO: 2) | Binds Fe at low pH |
| Transferrin (TF) | 118129942b1 | GCTGTCCCTGACAAAACGGT (SEQ ID NO: 3) GGTATTCTCGTGCTCTGACAC (SEQ ID NO: 4) | Binds Fe at neutral pH |
| Tf receptor 1 | 291045184b1 | GATCAAGCCAGATCAGCATTCT (SEQ ID NO: 5) GTGTATGACAATGGTTCCCCAC (SEQ ID NO: 6) | Internalizes transferrin |
| Tf receptor 2 | 113204629b1 | CGTTGGGGTCTACTTCGGAGA (SEQ ID NO: 7) AGATGGTCTGAGAGGGTCTTG (SEQ ID NO: 8) | Internalizes transferrin |
| Lf receptor/ intelectin 1 | 118130045b1 | CAGCACTTGGGACATAATCTGT (SEQ ID NO: 9) TCCTTCTCCGTATTTCACTGGG (SEQ ID NO: 10) | Internalizes lactoferrin |
| Lipocalin-1-Human | 32455234b1 | ATGTGTCAGGGACGTGGTATC (SEQ ID NO: 11) CCGATTCCAGATTCATCTCAGG (SEQ ID NO: 12) | Binds fungal siderophores |
| Heme Binding Protein | | | |
| Haptoglobin | 254910958b1 | GCACTTGGTTCGCTATCGCT (SEQ ID NO: 13) GCCCGTAGTCTGTAGAACTGT (SEQ ID NO: 14) | Binds hemoglobin |
| Hemopexin | 160358828b1 | AGCAGTGGCGCTAAATATCCT (SEQ ID NO: 15) CAACTCTCCCGTTGGCAGTA (SEQ ID NO: 16) | Binds heme |
| Siderophore Binding | | | |
| Lipocalin-1 | 32455234b | ATGTGTCAGGGACGTGGTATC (SEQ ID NO: 17) CCGATTCCAGATTCATCTCAGG (SEQ ID NO: 18) | Binds fungal siderophores |
| Lipocalin-2 | 34328048b1 | GCAGGTGGTACGTTGTGGG (SEQ ID NO: 19) CTCTTGTAGCTCATAGATGGTGC (SEQ ID NO: 20) | Binds bacterial siderophores |

TABLE 2-continued

Primers sequence and protein function

| Primer | Source (PB ID) | Sequence | Protein Function |
| --- | --- | --- | --- |
| Hepcidin Signaling | | | |
| Interleukin 6 | 13624310b1 | CTGCAAGAGACTTCCATCCAG (SEQ ID NO: 21) AGTGGTATAGACAGGTCTGTTGG (SEQ ID NO: 22) | Induces HAMP* synthesis |
| HFE | 145966687b1 | CGGGCTGCCTTTGTTTGAG (SEQ ID NO: 23) CTGGCTTGAGGTTTGCTCC (SEQ ID NO: 24) | Signal transduction □HAMP |
| BMP-2 | 71896668b1 | TCTTCCGGGAACAGATACAGG (SEQ ID NO: 25) TGGTGTCCAATAGTCTGGTCA (SEQ ID NO: 26) | Amplifies HAMP synthesis |
| BMP-4 | 121949822b1 | ATTCCTGGTAACCGAATGCTG (SEQ ID NO: 27) CCGGTCTCAGGTATCAAACTAGC (SEQ ID NO: 28) | Amplifies HAMP synthesis |
| BMP6 | 118131176b1 | GCGGGAGATGCAAAAGGAGAT (SEQ ID NO: 29) ATTGGACAGGGCGTTGTAGAG (SEQ ID NO: 30) | Amplifies HAMP synthesis |
| alk1-BMPR type 1a | 133891829b1 | TGGCACTGGTATGAAATCAGAC (SEQ ID NO: 31) CAAGGTATCCTCTGGTGCTAAAG (SEQ ID NO: 32) | BMP* receptor |
| alk2-BMPR type 1b | 41053831b1 | CCTCGGCCCAAGATCCTAC (SEQ ID NO: 33) CCTAGACATCCAGAGGTGACA (SEQ ID NO: 34) | BMP* receptor |
| actrIIA-BMPR type 2 | 145966831b1 | GTGTTATGGTCTGTGGGAGAAAT (SEQ ID NO: 35) AAAGCGGTACGTTCCATTCTG (SEQ ID NO: 36) | BMP* receptor |
| Hemojuvelin | 166295197b1 | ATGGGCCAGTCCCCTAGTC (SEQ ID NO: 37) CAGCGGAGGATCTTGCACT (SEQ ID NO: 38) | BMPR signaling |
| Hepcidin | Blood 2010 | CTGAGCAGCACCACCTATCTC (SEQ ID NO: 39) TGGCTCTAGGCTATGTTTTGC (SEQ ID NO: 40) | Degrades ferroportin |
| Ferroportin | 124248584b1 | TGGAACTCTATGGAAACAGCCT (SEQ ID NO: 41) TGGCATTCTTATCCACCCAGT (SEQ ID NO: 42) | Exports iron from cells |
| Housekeeping Gene | | | |
| B-actin-Mouse | 6671509a1 | GGCTGTATTCCCCTCCATCG (SEQ ID NO: 43) CCAGTTGGTAACAATGCCATGT (SEQ ID NO: 44) | Housekeeping gene |
| β-actin-Human | 144922730c1 | GTCTGCCTTGGTAGTGGATAATG (SEQ ID NO: 45) TCGAGGACGCCCTATCATGG (SEQ ID NO: 46) | Housekeeping gene |

*BMP: bone morphogenetic protein, HAMP: hepcidin, HFE: human hemochromatosis protein, Tf: transferrin Quantification of Iron Content in Mouse Serum Whole blood was obtained from mice by retro-orbital bleeding, and serum was recovered following blood coagulation. An iron assay kit (ABCAM, Cambridge, Mass.) was subsequently used to ascertain the concentration of $Fe^{2+}$ and $Fe^{3+}$ in the serum per manufacturer's instructions. Briefly, 25 µl of serum was added to 75 µl iron assay buffer and 5 µl iron reducer, which reduces $Fe^{3+}$ to $Fe^{2+}$. Next, 100 µl of the iron-probe solution was added yielding a $Fe^{2+}$-ferene S complex that absorbs light at 593 nm. Spectrophotometry was used to detect absorbance at this wavelength.

In Vitro Human Neutrophil:Hyphae Growth Inhibition Assay

Human neutrophils were isolated from normal, healthy donors using Ficoll-Paque Plus (GE) density centrifugation as described. Isolated conidia from each *A. fumigatus* mutant were cultured in 200 µl SDA media (12,500/well) in black-wall 96 well plates with an optically clear bottom (CoStar 3720) until early germ tubes were observed (4-6 h). Wells were washed twice with sterile $ddH_2O$ and incubated 16 h with either RPMI media (+Control), PBS (−Control), or a sublethal dose of human peripheral blood neutrophils in RPMI ($0.5-1*10^5$/well). At 16 h post-exposure, plates were washed once and stained with 50 µl calcofluor white stain (Binds chitin; Fluka 18909) for 5 min in the dark. Subsequently, plates were washed three times with ddH2O and quantified by fluorometry (360/440 nm; Synergy HT; Biotek).

Statistical Analysis

Statistical analysis was performed for each experiment using one way ANOVA with a tukey posthoc analysis using Prism software (GraphPad Software Inc, La Jolla, Calif.). A p value <0.05 was considered significant.

Results

Dectin-1 and IL-6 Regulate Local and Systemic Endogenous Host Iron-Sequestration Pathways Under homeostatic conditions, iron is bound to hemoglobin, transferrin, and ferritin; however, following infection, intracellular labile iron pools are released, including ferritin and heme-containing proteins. In addition, lysed red blood cells release hemoglobin and heme, which can be utilized by microbial pathogens. Also following infection, there is rapid production of pro-inflammatory and chemotactic cytokines that recruit neutrophils and macrophages that release preformed or de novo synthesized iron sequestering proteins.

To determine if fungal infection of the cornea initiates an iron-sequestration response, we infected C57BL/6, Dectin-$1^{-/-}$, and IL-$6^{-/-}$ mice intrastromally with *A. fumigatus* dsRed conidia as described. After 10 h, corneas were dissected and homogenized, and IL-6 was quantified by ELISA. FIG. 1A shows increased IL-6 in the corneas of infected compared with naïve C57BL/6 mice; however, IL-6 was not detected in corneas of infected Dectin-$1^{-/-}$ mice. Serum IL-6 was also increased 400-fold in infected compared with naïve C57BL/6 and infected Dectin-$1^{-/-}$ corneas (FIG. 1B). As hepcidin expression is induced by IL-6, we examined hepcidin expression in livers of infected C57BL/6 and IL-$6^{-/-}$ mice at 24 h post-infection. FIG. 1C shows that hepcidin expression was elevated 10-fold in infected compared with naïve C57BL/6 mice, whereas expression was significantly lower in infected IL-$6^{-/-}$ mice.

Prior to examining de novo transcription of iron-sequestering genes during infection we first quantified the number of neutrophils infiltrating C57BL/6 and IL-$6^{-/-}$ infected corneas by flow cytometry using the neutrophil specific NIMP-R14 monoclonal antibody. As shown in FIG. 1D, there was no significant difference in neutrophil numbers between infected mice at this time point indicating similar cellular populations in the corneas of C57BL/6 and IL-$6^{-/-}$ mice. Subsequently, RNA was isolated from C57BL/6 and IL-$6^{-/-}$ corneas at 24 h post-infection, and gene expression was measured by Q-PCR.

Compared with naïve C57BL/6 corneas, expression of the iron chelating protein transferrin (TF) was up-regulated 10-fold, transferrin receptor 2 (TR2) expression was up regulated 400-fold, and lactoferrin receptor/intelectin-1 (LR) was elevated 3-fold in infected corneas (FIG. 1E). Expression of these genes was not elevated in infected IL-$6^{-/-}$ corneas. Lactoferrin and transferrin receptor 1 expression were not elevated in C57BL/6 corneas, most likely due to these proteins being pre-formed in neutrophils.

During infection, lysed cells release heme, which microbes can utilize as a source of iron. To restrict microbial access to heme, mammals produce hemopexin that binds to heme and haptoglobin which binds hemoglobin. FIG. 1E also shows that expression of hemopexin (Hpx) and haptoglobin (HptG) are up-regulated 200-fold during infection compared with naïve mice, and that expression is lower in infected IL-$6^{-/-}$ corneas.

In a low iron environment, microbial siderophores bind iron with high affinity and are subsequently internalized through siderophore receptors on the fungal membrane. Humans encode lipocalin-1 (Lcn-1) and lipocalin-2 (Lcn-2), whereas mice only express Lcn-2. Both Lcn-1 and Lcn-2 bind to bacterial siderophores, but only Lcn-1 has been shown to bind to fungal hydroxymate-type siderophores. We found that in infected murine corneas, Lcn-2 expression is elevated 600-fold (FIG. 1E).

Although hepcidin is produced systemically by the liver, it is also produced by neutrophils and monocytes after stimulation with IL-6 or by iron-bound transferrin-mediated activation of the transferrin receptor 2/human hemochromatosis protein (HFE) complex. Further, hepcidin induction is synergistically increased by bone-morphogenetic protein (BMP) mediated activation and signaling through a hemojuvelin/BMP receptor complex. FIG. 1E shows that many of the proteins involved in non-inflammatory induction of hepcidin are up regulated at 24 h post-infection including: HFE protein (200-fold), BMP2 (200-fold), BMP-4 (30 fold), BMP-6 (10-fold), the BMP receptors: alk1 (2000-fold) alk2 (300-fold), actr2A (300-fold), and hemojuvelin (300-fold). Interestingly, local hepcidin transcript is only 2-fold up-regulated at 24 h post-infection. In addition, ferroportin transcripts are up-regulated 250-fold during infection (FIG. 1E), which may be a secondary response following hepcidin-mediated ferroportin degradation.

Given that we identified IL-6 as the main inducer of hepatic hepcidin during infection, we also examined if IL-6 mediates the iron sequestration response in the cornea. FIG. 1E shows that the transcription of all the hepcidin genes analyzed, except BMP-4, were significantly lower in infected IL-$6^{-/-}$ mice compared to infected C57BL/6 mice.

Given that human neutrophils store Lcn-2 in secondary granules, we reasoned that human neutrophils also produce Lcn-1 during fungal infection. We therefore incubated human neutrophils from three volunteers with *A. fumigatus* crude hyphal extract, and examined human Lcn-1 expression by Q-PCR. As shown in FIG. 1F, Lcn-1 gene expression was detected in human neutrophils in the presence or absence of crude hyphal extract, indicating constitutive RNA expression.

Taken together, these results indicate that following fungal infection of the cornea, Dectin-1 dependent IL-6 production induces local and systemic host responses that limit microbial access to iron.

Iron Availability Regulates Hyphal Growth and the Severity of A. fumigatus Infection Given that fungal infection initiates an iron sequestration response, we next examined if iron availability regulates fungal growth during infection. To enhance fungal access to iron during infection, mice were injected intraperitoneally with Fe-dextran (5 mg) or deferroxamine (5 mg), which is an ironchelating xenosiderophore that can be utilized by A. fumigatus. Twenty four hours after the last injection, RFP-expressing A. fumigatus (Af-dsRed) conidia were injected into the corneal stroma of C57BL/6 mice. After 24 h, total serum iron was quantified in treatment and control groups. FIG. 2A shows that serum iron levels in infected mice were reduced 2-fold compared with naïve mice, indicating systemic iron-sequestration during inflammation. In contrast, mice given systemic Fe-dextran, but not deferroxamine had significantly elevated serum iron compared to vehicle-treated mice. Despite the difference in serum iron levels, FIG. 2B-D show that Fe-dextran and deferroxamine-treated mice had significantly increased fungal mass and CFU compared with infected mice receiving vehicle alone. FIGS. 2B, E, and F shows that corneal opacification was also increased in Fe-dextran and deferroxamine-treated mice compared to vehicle-treated mice. The increased fungal growth in deferroxamine treated mice is likely due to its role as a xenosiderophore that can be used by Aspergillus for iron acquisition.

To examine the converse role of iron limitation in fungal growth during infection, C57BL/6 corneas were infected with A. fumigatus dsRed conidia as described, and the iron chelating protein lactoferrin was added topically (10.4 µg in 8 µl) at 0 h and 6 h post-infection. As shown in FIG. 2G-I, infected corneas given topical lactoferrin had significantly less fungal mass (dsRed) and CFU at 24 h post-infection compared with those given vehicle.

Taken together these studies demonstrate that fungal growth in the cornea is dependent on increased free iron or bio-available iron.

Siderophores and Detection of Low Iron Concentrations but not Reductive Iron Assimilation is Required for Fungal Growth During Infection Given that fungal growth during infection is enhanced by the exogenous xenosiderophore deferroxamine, we next examined the role of endogenous fungal siderophores using A. fumigatus, F. oxysporum, and Alternaria brassicicola iron acquisition mutants. The A. fumigatus ΔsidA mutant does not synthesize extracellular or intracellular siderophores, whereas the ΔhapX strain lacks the transcription factor HapX that is activated by low iron concentrations and mediates upregulation of genes involved in iron acquisition including siderophores and repression of iron-dependent pathways.

FIG. 3A shows no significant difference in fungal growth in media alone between the parent (WT) strain and the ΔsidA and ΔhapX mutants, indicating that there is no effect of these mutations on fungal growth in the presence of an exogenous source of iron. In contrast, when human neutrophils were added, fungal growth of the ΔsidA and ΔhapX mutants was significantly less than the WT parental strain, indicating that adaptation to iron starvation and siderophores, which requires SidA and HapX is essential for survival in the presence of neutrophils.

Consistent with a role for these genes in virulence, we found that at 48 h post-infection, corneas infected with the A. fumigatus mutant strains ΔsidA or ΔhapX had significantly lower CFU compared with the parent strain (FIG. 3B). In contrast, although the ΔftrA mutant lacks a membrane-bound iron transport channel protein and is therefore deficient in cellular uptake of environmental iron, there was no significant difference in CFU in this mutant, indicating that this transporter protein is not essential for fungal growth in vivo. Consistent with the higher CFU data, FIGS. 3C, E, and F show that mice infected with the ΔsidA or ΔhapX mutants have significantly less corneal opacification than the parent A. fumigatus strain, whereas the ΔftrA mutant was not significantly different. Histological analysis shows a pronounced cellular infiltrate and fungal hyphae in the corneas of mice infected with the parent strain, whereas no hyphae were detected in ΔsidA infected corneas, indicating that these mutants are unable to germinate in the cornea (FIG. 3D). As with A. fumigatus, mice infected with the F. oxysporum ΔhapX strain also exhibit significantly lower CFU than the parent strain at 48 h postinfection (FIG. 3G), and A. brassicicola siderophore mutants have significantly less CFU than the parent strains. FIG. 3H-J demonstrate that mice infected with the F. oxysporum ΔhapX strain also exhibit significantly less corneal opacification compared to the parental strain.

Taken together, these data indicate that siderophores have a critical role in fungal growth during infection, whereas reductive iron assimilation is not essential.

Extracellular Siderophores are Required for Fungal Infection

The A. fumigatus siderophore biosynthesis pathway originates with the sidA gene, which encodes ornithine-N5-oxygenase, resulting in conversion of ornithine to N5-hydroxyornithine (FIG. 4A). Utilizing this essential precursor, the siderophore biosynthesis pathway leads to either extracellular or intracellular siderophores. A. fumigatus synthesizes the extracellular siderophores fusarinine C (FusC) and triacetylfusarinine C (TAFC), and the intracellular siderophores ferricrocin (FC) and hydroxyferricrocin (HFC). The sidF gene encodes an N5 transacylase that incorporates anyhydromevalonyl CoA into N5-hydroxyornithine forming an extracellular siderophore precursor. The sidD gene encodes a non-ribosomal peptide synthase that further modifies the extracellular siderophore precursor yielding FusC, which is either secreted or tri-acylated by the sidG gene product to generate TAFC, which is a more stable, secreted product. Alternatively, N5 hydroxyornithine can be acetylated and modified by the sidC gene product to form the intracellular siderophores FC or HFC.

To determine the relative contribution of intracellular versus extracellular siderophores in fungal keratitis, corneas were infected with the ΔsidF and ΔsidC mutants. FIG. 4B shows that CFU from corneas infected with the ΔsidF mutant that leads to extracellular siderophore production was significantly lower than those infected with WT A. fumigatus, having a similar CFU as ΔsidA mutants. In contrast, ΔsidC mutants that regulate production of intracellular siderophores were not significantly different from the parent strain. Consistent with this finding, corneas infected with ΔsidF had significantly lower cornea opacity area and intensity values compared with mice infected with WT A. fumigatus, whereas ΔsidC mutants were not significantly different (FIG. 4C-E). Together, these findings indicate that extracellular not intracellular siderophores are essential for fungal growth in the cornea and development of keratitis.

To determine the relative contribution of the extracellular siderophores FusC and TAFC, we infected corneas with ΔsidD mutants, which do not produce extracellular siderophores or ΔsidG mutants, which produce FusC but not TAFC, and compared them with the parent *A. fumigatus* strain that produces both FusC and TAFC (34). FIG. 4B shows that mice infected with ΔsidD mutants had significantly lower CFU compared with WT *A. fumigatus*, whereas ΔsidG were not significantly different. Corneal opacification scores reflected the CFU data, with ΔsidD but not ΔsidG mutants having significantly less opacification than WT *A. fumigatus* (FIG. 4C-E). These findings indicate that sidD-mediated synthesis of FusC but not sidG mediated synthesis of TAFC is essential for fungal growth in vivo. Extracellular siderophore mutants of *Alternaria brassicicola* also have impaired growth during infection (data not shown).

Together, these data clearly demonstrate that extracellular rather than intracellular siderophores are essential for *Aspergillus* and *Alternaria* growth during tissue infection, and that even though TAFC is reportedly more stable, FusC production is sufficient to maintain fungal growth in vivo.

Mevalonate Incorporation into Extracellular Siderophores is Required for Fungal Infection Fungal extracellular siderophore biosynthesis requires HMG-CoA reductase-dependent synthesis of the precursor mevalonate. The *Aspergillus* genes sidI and sidH encode a CoA ligase and an enoyl-CoA-hydratase, respectively, which convert mevalonic acid to anhydromevalonyl CoA and incorporate this precursor through the sidF-D-G pathway into the structure of fusarinine C and TAFC (FIG. 5A).

Figure 5B:
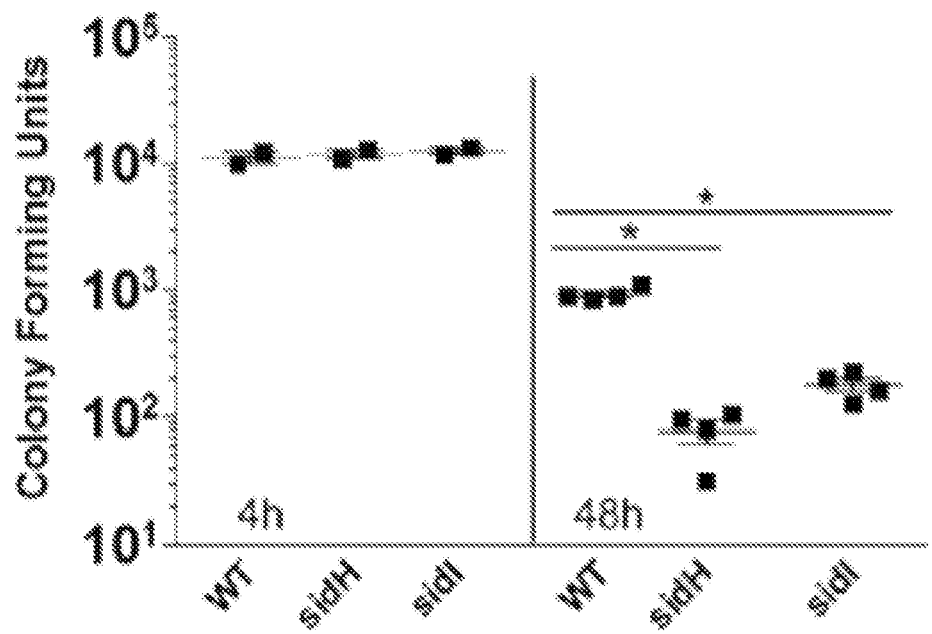
Figure 5C:
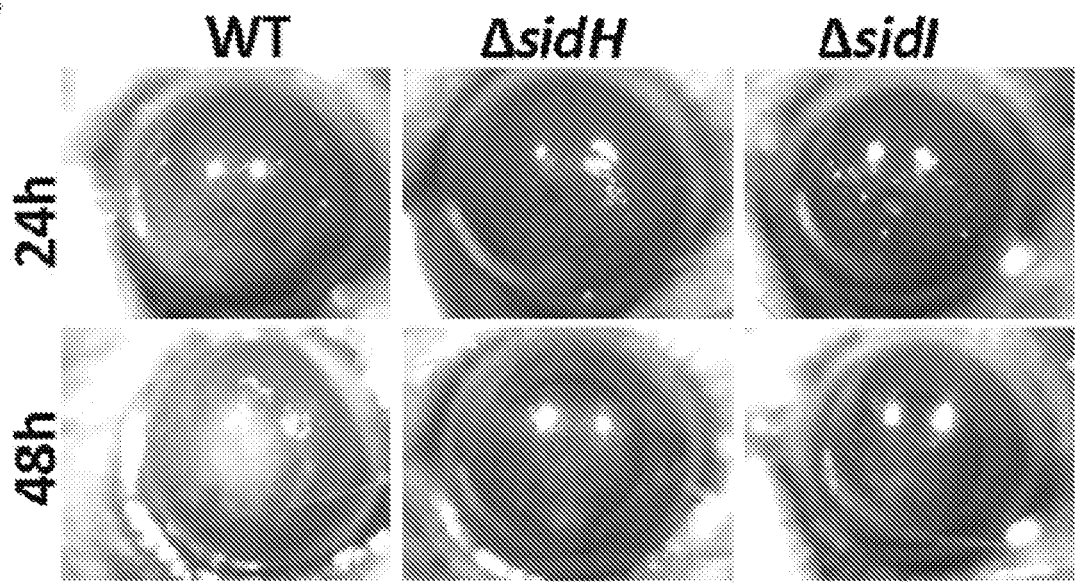
Figure 5D:
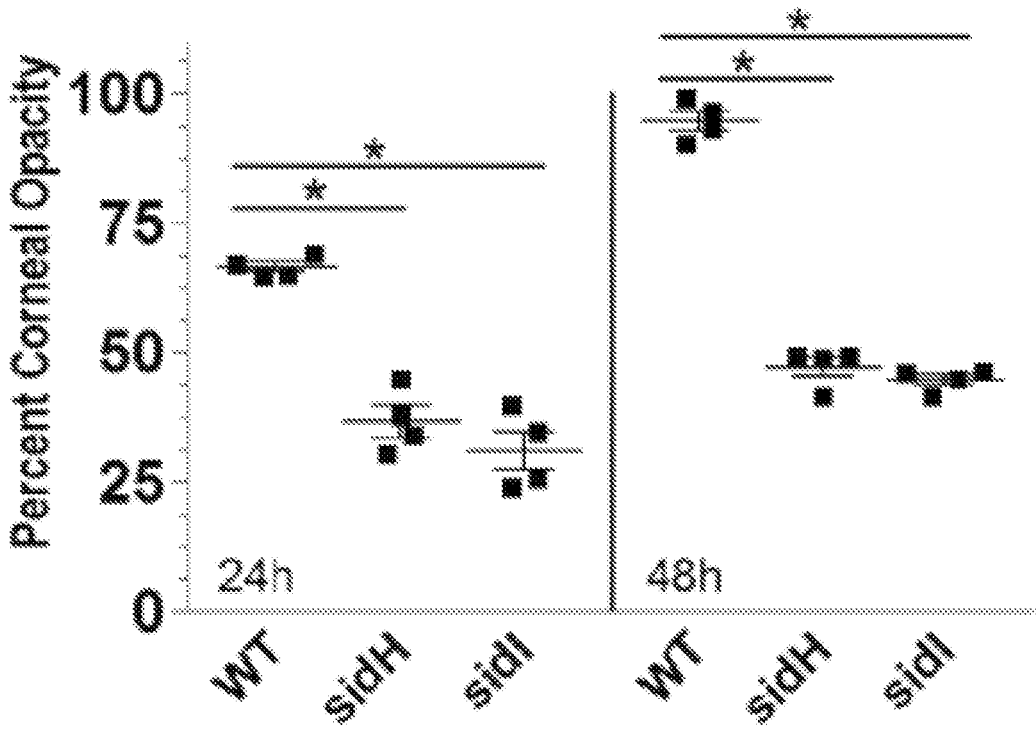
Figure 5E:
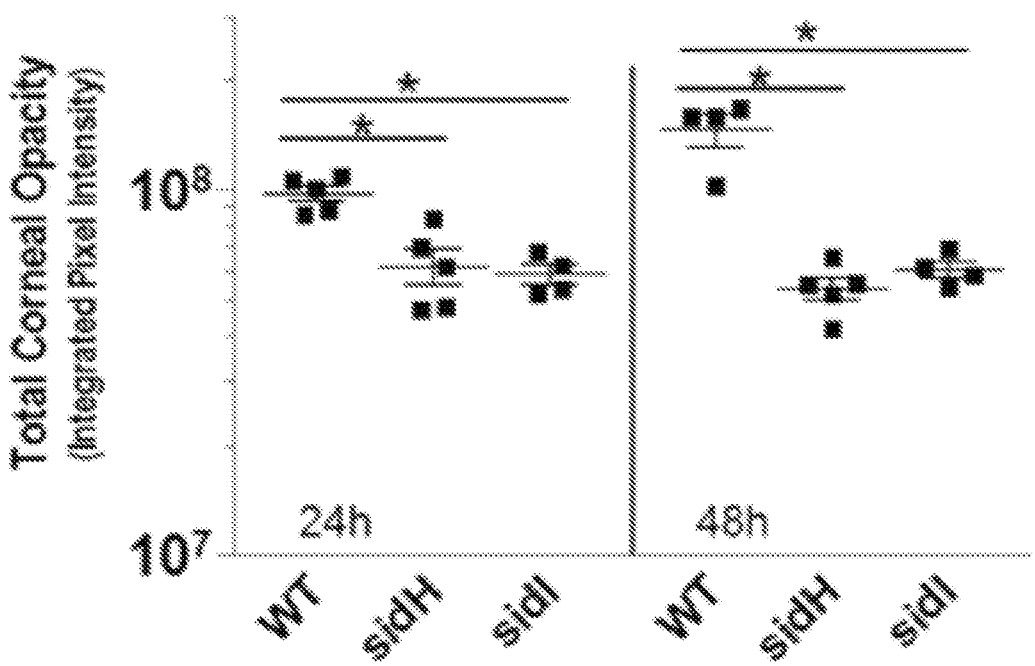
Figure 9:
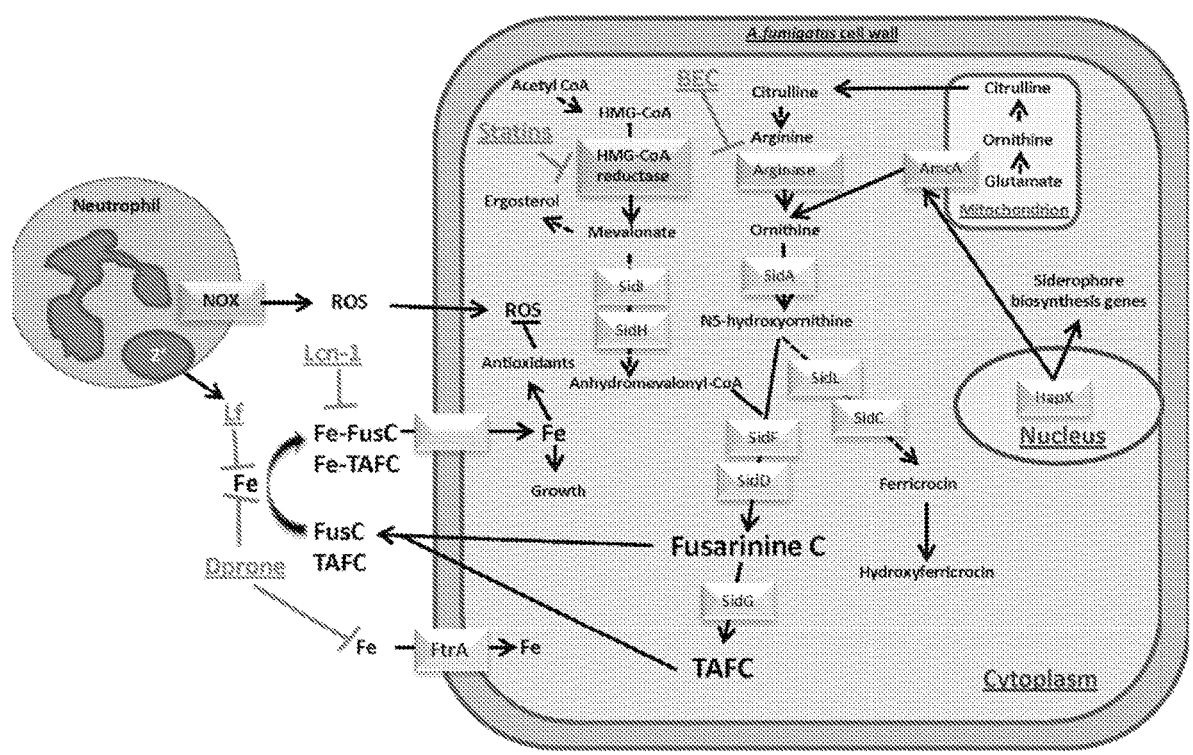
FIG. 9 illustrates a schematic drawing showing the battle for iron between the mammalian host and fungi. BEC—boronoethyl L cysteine, Defox—deferroxamine, Dprone—deferiprone, Fe—iron, Fus C—fusarinine C, HMGCoA—3 hydroxy—3methylglutaryl-coenzyme, Lcn-1—lipocalin 1, Lf—lactoferrin, NOX—nicotinamide adenine dinucleotide phosphate oxidase, ROS—reactive oxygen species, TAFC—triacetyl fusarinine C.

To determine if this pathway is essential for fungal growth during tissue infection, C57BL/6 mice were infected with *A. fumigatus* mutant strains ΔsidH and ΔsidI and examined as before. FIG. 5B shows that mice infected with ΔsidH or ΔsidI exhibit significantly less CFU than mice infected with the WT strain, indicating that mevalonate incorporation into extracellular siderophores is essential for fungal growth during tissue infection. Further, mice infected with either ΔsidH or ΔsidI exhibit significantly less cornea opacity at all time-points compared to mice infected with WT *A. fumigatus* (FIG. 5C-E).

Lipocalin-1 Sequesters Fungal Siderophores and Restricts Fungal Growth During Infection Humans produce two lipocalins with siderophore binding activity. Lipocalin-1 (Lcn-1) binds to a wide range of bacterial and fungal hydroxymate-type siderophores, whereas Lcn-2 binds only a few catechol-type bacterial siderophores but not fungal siderophores. We therefore examined the role of Lcn-1 on *A. fumigatus* using the same assays as above. FIG. 6B shows significantly less fungal growth in the presence of 40 μg/ml or 4 μg/ml Lcn-1, and that *A. fumigatus* growth in the presence of neutrophils and 4 μg/ml Lcn-1 was significantly less than in the presence of neutrophils alone or with Lcn-1 alone. FIG. 6C-E show that mice treated with topical Lcn-1 (16 μg/8 μl) at 0 h and 6 h after infection had significantly less fungal dsRed and CFU compared with infected mice in the absence of exogenous Lcn-1. These findings indicate that sequestering fungal siderophores with topical Lcn-1 inhibits fungal growth in vivo.

Arginase Inhibitors Block Fungal Growth During Infection

Siderophore production by filamentous fungi requires the precursor amino acid ornithine (FIG. 7A), which is produced in the mitochondria and exported to the cytoplasm through the ornithine transporter AmcA. Alternatively, ornithine can be produced directly in the cytosol from arginine by the enzyme arginase. To examine the role of arginase in fungal killing by neutrophils, *A. fumigatus* was incubated with human neutrophils in the presence of the arginase inhibitors: Nω-hydoxy-norNOHA (nNOHA) or S-2-boronoethyl L-cysteine (BEC).

FIG. 7B shows that fungal growth in the presence of 100 μM nNOHA or 10 μM BEC was significantly lower than in RPMI alone. Fungal growth was also significantly lower in the presence of 100 μM BEC when incubated with neutrophils compared with neutrophils alone, whereas incubation with nNOHA was not significantly different from neutrophils alone. To examine the role of arginase inhibitors on fungal growth during infection, we infected C57BL/6 mice as described above and at 0 and 6 h post-infection applied 8 μl of a topical formulation of vehicle or BEC (40 μg in 8 μl) to infected corneas. FIG. 7C-E show that mice treated with BEC had significantly lower fungal dsRed and CFU at 24 h post-infection than control, infected mice. Although arginase is also involved in the mammalian urea cycle, there were no apparent ill effects on the cornea following topical BEC treatment.

These data indicate that targeting fungal arginase, which mediates ornithine and siderophore biosynthesis, facilitates neutrophil killing in vitro and inhibits fungal growth during infection.

Topical Simvastatin and Deferiprone Inhibit Fungal Infection

As shown in FIG. 5, *Aspergillus* SidI and SidH proteins incorporate mevalonate into the structure of extracellular siderophores and are essential for fungal growth in the cornea. HMG CoA reductase is required for mevalonate production and can be targeted by statins resulting in decreased siderophore biosynthesis (FIG. 8A). To determine the effect of blocking this pathway on fungal growth, *A. fumigatus* and *Fusarium* oxysporum were incubated in media with simvastatin and lovastatin, or with the iron chelators, deferiprone and deferroxamine.

As shown in FIG. 8B, there was significantly less growth of *A. fumigatus* following incubation with simvastatin, lovastatin and deferiprone, but not deferroxamine, thereby demonstrating a direct effect of statins and deferiprone on fungal growth. Similar results were obtained with *Fusarium oxysporum* (FIG. 8C). When incubated in the presence of human neutrophils, *A. fumigatus* growth was also inhibited in cells incubated with simvastatin, lovastatin, or deferiprone (FIG. 8D). In contrast, fungi incubated with the xenosiderophore deferroxamine showed growth similar to incubation with neutrophils alone. (FIG. 8D). To ascertain if statins can restrict fungal growth during infection, infected mice were given topical simvastatin, deferiprone, or deferroxamine at the time of infection and after 6 h. As shown in FIGS. 8E and F, mice treated with simvastatin and deferiprone exhibited significantly less fungal dsRed emission compared to vehicle-treated mice. In contrast, there was significantly increased fungal dsRed in deferroxamine-treated mice compared to vehicle-treated mice (FIG. 8E, F). FIG. 8G shows similar responses when CFU were measured.

Given that simvastatin inhibits fungal siderophore synthesis whereas deferiprone chelates free iron, we hypothesized that dual therapy would have a synergistic or additive effect on fungal growth. As shown in FIGS. 8E and F, mice treated with both simvastatin and deferiprone exhibited significantly lower fungal dsRed than mice treated with simvastatin alone. FIG. 8G shows that these mice also exhibited significantly decreased CFU per cornea compared to single drug treatment or vehicle-treated mice.

In addition to regulating siderophore synthesis, HMG-CoA reductase is also important in ergosterol production, which is incorporated into the fungal cell membrane. To determine the effect of simvastatin on the siderophore pathway, infected mice were treated with simvastatin and deferroxamine. As shown in FIG. 8E-G, mice treated with simvastatin and deferroxamine exhibit increased fungal dsRed and CFU compared with mice given simvastatin alone, indicating that simvastatin is targeting siderophore biosynthesis in addition to ergosterol synthesis. These findings clearly demonstrate that topical statins and iron chelation can block fungal infection.

Together, this example identifies specific host iron-chelating and fungal iron-acquisition mediators that regulate fungal growth, and demonstrate that therapeutic inhibition of fungal iron acquisition can be utilized in an effective method of treating treat topical fungal infections.

From the above description, those skilled in the art will perceive improvements, changes and modifications. Such improvements, changes and modifications within the skill of the art are intended to be covered by the appended claims. All references, publications, and patents cited in the present application are herein incorporated by reference in their entirety.

Having described the invention, we claim:

1. A method of treating a skin/nail or mucosal fungal infection in a subject comprising:
topically administering to the subject a therapeutically effective amount of an iron chelator and a siderophore biosynthesis inhibitor to treat the skin/nail or mucosal fungal infection in the subject.

2. The method of claim 1, the iron chelator comprising lactoferrin.

3. The method of claim 1, the iron chelator comprising a 3,5-diphenyl-1,2,4-triazole derivative or a salt thereof.

4. The method of claim 3, the 3,5-diphenyl-1,2,4-triazole derivative selected from the group consisting of deferasirox, deferiprone, deferitrin, deferoxamine or a salt thereof.

5. The method of claim 1, the iron chelator comprising deferiprone.

6. The method of claim 1, the siderophore biosynthesis inhibitor comprising an arginase inhibitor.

7. The method of claim 6, the arginase inhibitor selected from the group consisting of (S)-(2-Boronoethyl)-L-cysteine (BEC), 2(S)-amino-6-boronohexanoic acid (ABH), $N^G$-Hydroxy-L-arginine (NOHA), $N^\omega$-Hydroxy-nor-L-arginine (nor-NOHA) and DL-alpfa-Difluoromethylornithine (DFMO).

8. The method of claim 6, the arginase inhibitor comprising (S)-(2-Boronoethyl)-L-cysteine (BEC).

9. The method of claim 1, the siderophore biosynthesis inhibitor comprising a statin.

10. The method of claim 9, the statin selected from the group consisting of simvastatin, mevistatin, lovastatin, pravastatin, fluvastatin, atorvastatin and cerivastatin.

11. The method of claim 1, further comprising topically administering to the subject a therapeutically effective amount of a siderophore binding protein to treat the fungal infection in the subject.

12. The method of claim 11, the siderophore binding protein comprising lipocalin-1.

13. The method of claim 1, the fungal infection selected from an *Alternaria*, *Aspergillus*, *Candida*, *Curvularia*, *Fusarium*, or *Histoplasma* fungal infection.

14. The method of claim 1, the subject not having a fungal infection, but being at risk of developing a fungal infection.

15. The method of claim 1, wherein the subject is a neutropenic subject.

16. The method of claim 1, the iron chelator and siderophore biosynthesis inhibitor being administered to the subject in an ophthalmic preparation.

17. The method of claim 1, the iron chelator and the siderophore biosynthesis inhibitor being administered to the subject in conjunction with one or more additional therapeutic agents.

18. The method of claim 1, wherein the iron chelator is deferiprone and the siderophore biosynthesis inhibitor is a statin.

19. The method of claim 17, the one or more additional therapeutic agents comprising an antibiotic, antiviral or antifungal agent.

* * * * *

SEQUENCE LISTING

<160> NUMBER OF SEQ ID NOS: 46

<210> SEQ ID NO 1
<211> LENGTH: 21
<212> TYPE: DNA
<213> ORGANISM: Artificial Sequence
<220> FEATURE:
<223> OTHER INFORMATION: Synthetic Constructs

<400> SEQUENCE: 1
ccgctcagtt gtgtcaagaa a                                              21

<210> SEQ ID NO 2
<211> LENGTH: 21
<212> TYPE: DNA
<213> ORGANISM: Artificial Sequence
<220> FEATURE:
<223> OTHER INFORMATION: Synthetic Constructs

<400> SEQUENCE: 2
catggcatca gctctgtttg t                                              21

<210> SEQ ID NO 3
<211> LENGTH: 20
<212> TYPE: DNA
<213> ORGANISM: Artificial Sequence
<220> FEATURE:
<223> OTHER INFORMATION: Synthetic Constructs

<400> SEQUENCE: 3
gctgtccctg acaaaacggt                                                20

<210> SEQ ID NO 4
<211> LENGTH: 21
<212> TYPE: DNA
<213> ORGANISM: Artificial Sequence
<220> FEATURE:
<223> OTHER INFORMATION: Synthetic Constructs

<400> SEQUENCE: 4
ggtattctcg tgctctgaca c                                              21

<210> SEQ ID NO 5
<211> LENGTH: 22
<212> TYPE: DNA
<213> ORGANISM: Artificial Sequence
<220> FEATURE:
<223> OTHER INFORMATION: Synthetic Constructs

<400> SEQUENCE: 5
gatcaagcca gatcagcatt ct                                             22

<210> SEQ ID NO 6

<211> LENGTH: 22
<212> TYPE: DNA
<213> ORGANISM: Artificial Sequence
<220> FEATURE:
<223> OTHER INFORMATION: Synthetic Constructs

<400> SEQUENCE: 6
gtgtatgaca atggttcccc ac                                              22

<210> SEQ ID NO 7
<211> LENGTH: 21
<212> TYPE: DNA
<213> ORGANISM: Artificial Sequence
<220> FEATURE:
<223> OTHER INFORMATION: Synthetic Constructs

<400> SEQUENCE: 7
cgttggggtc tacttcggag a                                               21

<210> SEQ ID NO 8
<211> LENGTH: 21
<212> TYPE: DNA
<213> ORGANISM: Artificial Sequence
<220> FEATURE:
<223> OTHER INFORMATION: Synthetic Constructs

<400> SEQUENCE: 8
agatggtctg agagggtctt g                                               21

<210> SEQ ID NO 9
<211> LENGTH: 22
<212> TYPE: DNA
<213> ORGANISM: Artificial Sequence
<220> FEATURE:
<223> OTHER INFORMATION: Synthetic Constructs

<400> SEQUENCE: 9
cagcacttgg gacataatct gt                                              22

<210> SEQ ID NO 10
<211> LENGTH: 22
<212> TYPE: DNA
<213> ORGANISM: Artificial Sequence
<220> FEATURE:
<223> OTHER INFORMATION: Synthetic Constructs

<400> SEQUENCE: 10
tccttctccg tatttcactg gg                                              22

<210> SEQ ID NO 11
<211> LENGTH: 21
<212> TYPE: DNA
<213> ORGANISM: Artificial Sequence
<220> FEATURE:
<223> OTHER INFORMATION: Synthetic Constructs

<400> SEQUENCE: 11
atgtgtcagg gacgtggtat c                                               21

<210> SEQ ID NO 12
<211> LENGTH: 22
<212> TYPE: DNA
<213> ORGANISM: Artificial Sequence
<220> FEATURE:
<223> OTHER INFORMATION: Synthetic Constructs

<400> SEQUENCE: 12
ccgattccag attcatctca gg                                              22

<210> SEQ ID NO 13
<211> LENGTH: 20
<212> TYPE: DNA
<213> ORGANISM: Artificial Sequence
<220> FEATURE:
<223> OTHER INFORMATION: Synthetic Constructs

<400> SEQUENCE: 13
gcacttggtt cgctatcgct                                                 20

<210> SEQ ID NO 14
<211> LENGTH: 21
<212> TYPE: DNA
<213> ORGANISM: Artificial Sequence
<220> FEATURE:
<223> OTHER INFORMATION: Synthetic Constructs

<400> SEQUENCE: 14
gcccgtagtc tgtagaactg t                                               21

<210> SEQ ID NO 15
<211> LENGTH: 21
<212> TYPE: DNA
<213> ORGANISM: Artificial Sequence
<220> FEATURE:
<223> OTHER INFORMATION: Synthetic Constructs

<400> SEQUENCE: 15
agcagtggcg ctaaatatcc t                                               21

<210> SEQ ID NO 16
<211> LENGTH: 20
<212> TYPE: DNA
<213> ORGANISM: Artificial Sequence
<220> FEATURE:
<223> OTHER INFORMATION: Synthetic Constructs

<400> SEQUENCE: 16
caactctccc gttggcagta                                                 20

<210> SEQ ID NO 17
<211> LENGTH: 21
<212> TYPE: DNA
<213> ORGANISM: Artificial Sequence
<220> FEATURE:
<223> OTHER INFORMATION: Synthetic Constructs

<400> SEQUENCE: 17
atgtgtcagg gacgtggtat c                                               21

<210> SEQ ID NO 18
<211> LENGTH: 22
<212> TYPE: DNA
<213> ORGANISM: Artificial Sequence
<220> FEATURE:
<223> OTHER INFORMATION: Synthetic Constructs

<400> SEQUENCE: 18
ccgattccag attcatctca gg                                              22

<210> SEQ ID NO 19
<211> LENGTH: 19
<212> TYPE: DNA

<213> ORGANISM: Artificial Sequence
<220> FEATURE:
<223> OTHER INFORMATION: Synthetic Constructs

<400> SEQUENCE: 19
gcaggtggta cgttgtggg                                                    19

<210> SEQ ID NO 20
<211> LENGTH: 23
<212> TYPE: DNA
<213> ORGANISM: Artificial Sequence
<220> FEATURE:
<223> OTHER INFORMATION: Synthetic Constructs

<400> SEQUENCE: 20
ctcttgtagc tcatagatgg tgc                                               23

<210> SEQ ID NO 21
<211> LENGTH: 21
<212> TYPE: DNA
<213> ORGANISM: Artificial Sequence
<220> FEATURE:
<223> OTHER INFORMATION: Synthetic Constructs

<400> SEQUENCE: 21
ctgcaagaga cttccatcca g                                                 21

<210> SEQ ID NO 22
<211> LENGTH: 23
<212> TYPE: DNA
<213> ORGANISM: Artificial Sequence
<220> FEATURE:
<223> OTHER INFORMATION: Synthetic Constructs

<400> SEQUENCE: 22
agtggtatag acaggtctgt tgg                                               23

<210> SEQ ID NO 23
<211> LENGTH: 19
<212> TYPE: DNA
<213> ORGANISM: Artificial Sequence
<220> FEATURE:
<223> OTHER INFORMATION: Synthetic Constructs

<400> SEQUENCE: 23
cgggctgcct ttgtttgag                                                    19

<210> SEQ ID NO 24
<211> LENGTH: 19
<212> TYPE: DNA
<213> ORGANISM: Artificial Sequence
<220> FEATURE:
<223> OTHER INFORMATION: Synthetic Constructs

<400> SEQUENCE: 24
ctggcttgag gtttgctcc                                                    19

<210> SEQ ID NO 25
<211> LENGTH: 21
<212> TYPE: DNA
<213> ORGANISM: Artificial Sequence
<220> FEATURE:
<223> OTHER INFORMATION: Synthetic Constructs

<400> SEQUENCE: 25
tcttccggga acagatacag g                                                 21

<210> SEQ ID NO 26
<211> LENGTH: 21
<212> TYPE: DNA
<213> ORGANISM: Artificial Sequence
<220> FEATURE:
<223> OTHER INFORMATION: Synthetic Constructs

<400> SEQUENCE: 26
tggtgtccaa tagtctggtc a                                      21

<210> SEQ ID NO 27
<211> LENGTH: 21
<212> TYPE: DNA
<213> ORGANISM: Artificial Sequence
<220> FEATURE:
<223> OTHER INFORMATION: Synthetic Constructs

<400> SEQUENCE: 27
attcctggta accgaatgct g                                      21

<210> SEQ ID NO 28
<211> LENGTH: 23
<212> TYPE: DNA
<213> ORGANISM: Artificial Sequence
<220> FEATURE:
<223> OTHER INFORMATION: Synthetic Constructs

<400> SEQUENCE: 28
ccggtctcag gtatcaaact agc                                    23

<210> SEQ ID NO 29
<211> LENGTH: 21
<212> TYPE: DNA
<213> ORGANISM: Artificial Sequence
<220> FEATURE:
<223> OTHER INFORMATION: Synthetic Constructs

<400> SEQUENCE: 29
gcgggagatg caaaaggaga t                                      21

<210> SEQ ID NO 30
<211> LENGTH: 21
<212> TYPE: DNA
<213> ORGANISM: Artificial Sequence
<220> FEATURE:
<223> OTHER INFORMATION: Synthetic Constructs

<400> SEQUENCE: 30
attggacagg gcgttgtaga g                                      21

<210> SEQ ID NO 31
<211> LENGTH: 22
<212> TYPE: DNA
<213> ORGANISM: Artificial Sequence
<220> FEATURE:
<223> OTHER INFORMATION: Synthetic Constructs

<400> SEQUENCE: 31
tggcactggt atgaaatcag ac                                     22

<210> SEQ ID NO 32
<211> LENGTH: 23
<212> TYPE: DNA
<213> ORGANISM: Artificial Sequence
<220> FEATURE:

<223> OTHER INFORMATION: Synthetic Constructs

<400> SEQUENCE: 32
caaggtatcc tctggtgcta aag                                          23

<210> SEQ ID NO 33
<211> LENGTH: 19
<212> TYPE: DNA
<213> ORGANISM: Artificial Sequence
<220> FEATURE:
<223> OTHER INFORMATION: Synthetic Constructs

<400> SEQUENCE: 33
cctcggccca agatcctac                                               19

<210> SEQ ID NO 34
<211> LENGTH: 21
<212> TYPE: DNA
<213> ORGANISM: Artificial Sequence
<220> FEATURE:
<223> OTHER INFORMATION: Synthetic Constructs

<400> SEQUENCE: 34
cctagacatc cagaggtgac a                                            21

<210> SEQ ID NO 35
<211> LENGTH: 23
<212> TYPE: DNA
<213> ORGANISM: Artificial Sequence
<220> FEATURE:
<223> OTHER INFORMATION: Synthetic Constructs

<400> SEQUENCE: 35
gtgttatggt ctgtgggaga aat                                          23

<210> SEQ ID NO 36
<211> LENGTH: 21
<212> TYPE: DNA
<213> ORGANISM: Artificial Sequence
<220> FEATURE:
<223> OTHER INFORMATION: Synthetic Constructs

<400> SEQUENCE: 36
aaagcggtac gttccattct g                                            21

<210> SEQ ID NO 37
<211> LENGTH: 19
<212> TYPE: DNA
<213> ORGANISM: Artificial Sequence
<220> FEATURE:
<223> OTHER INFORMATION: Synthetic Constructs

<400> SEQUENCE: 37
atgggccagt cccctagtc                                               19

<210> SEQ ID NO 38
<211> LENGTH: 19
<212> TYPE: DNA
<213> ORGANISM: Artificial Sequence
<220> FEATURE:
<223> OTHER INFORMATION: Synthetic Constructs

<400> SEQUENCE: 38
cagcggagga tcttgcact                                               19

```
<210> SEQ ID NO 39
<211> LENGTH: 21
<212> TYPE: DNA
<213> ORGANISM: Artificial Sequence
<220> FEATURE:
<223> OTHER INFORMATION: Synthetic Constructs

<400> SEQUENCE: 39
ctgagcagca ccacctatct c                                              21

<210> SEQ ID NO 40
<211> LENGTH: 21
<212> TYPE: DNA
<213> ORGANISM: Artificial Sequence
<220> FEATURE:
<223> OTHER INFORMATION: Synthetic Constructs

<400> SEQUENCE: 40
tggctctagg ctatgttttg c                                              21

<210> SEQ ID NO 41
<211> LENGTH: 22
<212> TYPE: DNA
<213> ORGANISM: Artificial Sequence
<220> FEATURE:
<223> OTHER INFORMATION: Synthetic Constructs

<400> SEQUENCE: 41
tggaactcta tggaaacagc ct                                             22

<210> SEQ ID NO 42
<211> LENGTH: 21
<212> TYPE: DNA
<213> ORGANISM: Artificial Sequence
<220> FEATURE:
<223> OTHER INFORMATION: Synthetic Constructs

<400> SEQUENCE: 42
tggcattctt atccacccag t                                              21

<210> SEQ ID NO 43
<211> LENGTH: 20
<212> TYPE: DNA
<213> ORGANISM: Artificial Sequence
<220> FEATURE:
<223> OTHER INFORMATION: Synthetic Constructs

<400> SEQUENCE: 43
ggctgtattc ccctccatcg                                                20

<210> SEQ ID NO 44
<211> LENGTH: 22
<212> TYPE: DNA
<213> ORGANISM: Artificial Sequence
<220> FEATURE:
<223> OTHER INFORMATION: Synthetic Constructs

<400> SEQUENCE: 44
ccagttggta acaatgccat gt                                             22

<210> SEQ ID NO 45
<211> LENGTH: 23
<212> TYPE: DNA
<213> ORGANISM: Artificial Sequence
<220> FEATURE:
<223> OTHER INFORMATION: Synthetic Constructs
```

```
<400> SEQUENCE: 45
gtctgccttg gtagtggata atg                                              23

<210> SEQ ID NO 46
<211> LENGTH: 20
<212> TYPE: DNA
<213> ORGANISM: Artificial Sequence
<220> FEATURE:
<223> OTHER INFORMATION: Synthetic Constructs

<400> SEQUENCE: 46
tcgaggacgc cctatcatgg                                                  20
```